United States Patent
Kobayashi et al.

(10) Patent No.: US 10,677,783 B2
(45) Date of Patent: Jun. 9, 2020

(54) METHOD FOR EVALUATING EFFECT OF CYTOKINE ON METABOLIC ACTIVITY OF CYTOCHROME P450, AND DRUG SCREENING METHOD

(71) Applicant: Corning Incorporated, Corning, NY (US)

(72) Inventors: Kaoru Kobayashi, Chiba (JP); Hanaka Mimura, Chiba (JP); Kan Chiba, Chiba (JP); Yoko Ejiri, Kurashiki (JP); Masaya Hosoda, Kurashiki (JP); Satoru Ayano, Kurashiki (JP)

(73) Assignee: Corning Incorporated, Corning, NY (US)

( * ) Notice: Subject to any disclaimer, the term of this patent is extended or adjusted under 35 U.S.C. 154(b) by 278 days.

(21) Appl. No.: 14/431,986

(22) PCT Filed: Sep. 27, 2013

(86) PCT No.: PCT/JP2013/005770
§ 371 (c)(1),
(2) Date: Mar. 27, 2015

(87) PCT Pub. No.: WO2014/050139
PCT Pub. Date: Apr. 3, 2014

(65) Prior Publication Data
US 2015/0276716 A1 Oct. 1, 2015

(30) Foreign Application Priority Data

Sep. 27, 2012 (JP) ................................. 2012-213977
Sep. 27, 2012 (JP) ................................. 2012-213978

(51) Int. Cl.
| | | |
|---|---|---|
| *C12Q 1/26* | (2006.01) | |
| *C12Q 1/6876* | (2018.01) | |
| *G01N 33/50* | (2006.01) | |
| *G01N 33/573* | (2006.01) | |

(52) U.S. Cl.
CPC ........... *G01N 33/5041* (2013.01); *C12Q 1/26* (2013.01); *C12Q 1/6876* (2013.01); *G01N 33/5073* (2013.01); *G01N 33/573* (2013.01); *C12Q 2600/136* (2013.01); *C12Q 2600/158* (2013.01); *G01N 2333/485* (2013.01); *G01N 2333/525* (2013.01); *G01N 2333/5412* (2013.01); *G01N 2333/80* (2013.01); *G01N 2500/04* (2013.01); *G01N 2500/10* (2013.01)

(58) Field of Classification Search
None
See application file for complete search history.

(56) References Cited

U.S. PATENT DOCUMENTS 7,691,369 B2   4/2010 Kataoka et al.
2007/0122901 A1   5/2007 Morita et al.

FOREIGN PATENT DOCUMENTS

| JP | 5 260957 | 10/1993 |
|---|---|---|
| JP | 2005 27598 | 2/2005 |
| JP | 2008022743 A | 2/2008 |
| JP | 2010 148386 | 7/2010 |
| JP | 2010233538 A | 10/2010 |
| JP | 2012213977 A | 11/2012 |
| JP | 2012213978 A | 11/2012 |
| WO | 2005 038011 | 4/2005 |

OTHER PUBLICATIONS

Dickmann et al. Effects of IL-6 and an anti-IL-6 monoclonal antibody on drug-metabolizing enzymes in human hepatocyte culture. Drug Metabolism and Disposition, 2011; 39(8):1415-1422.*
Dickmann et al. Effects of Interleukin-6 (IL-6) and an Anti-IL-6 Monoclonal Antibody on Drug-Metabolizing Enzymes in Human Hepatocyte Culture. Drug Metabolism and Disposition, 2011; 39(8): 1415-1422.*
Kobayashi et al. Increased expression of drug-metabolizing enzymes in human hepatocarcinoma FLC-4 cells cultured on micro-space cell culture plates. Drug Metabolism Pharmacokinetics, 2012; 27(5): 478-185.*
Abdel-Razzak et al. Transforming Growth Factor-beta1 Down-regulates Basal and Polycyclic Aromatic Hydrocarbon-Induced Cytochromes P-450 1A1 and 1A2 in Adult Human Hepatocytes in Primary Culture. Molecular Pharmacology, 1994; 46:1100-1110 (Year: 1994).*
Nakamura et al. Evaluation of drug toxicity with hepatocytes cultured in a micro-space cell culture system. Journal of Bioscience and Bioengineering, 2011; 111(1): 78-84 (Year: 2011).*
Office Action dated Sep. 1, 2015 in Japanese Patent Application No. 2012-213977 (with English language translation).
Office Action dated Sep. 1, 2015 in Japanese Patent Application No. 2012-213978 (with English language translation).
Kaoru Kobayashi, et al., "Increased Expression of Drug-metabolizing Enzymes in Human Hepatocarcinoma FLC-4 Cells Cultured on Micro-space Cell Culture Plates" Drug Metab. Pharmacokinet, vol. 27, No. 5, 2012, pp. 478-485.
Renton, K.W., "Cytochrome P450 Regulation and Drug Biotransformation During Inflammation and Infection", Current Drug Metabolism, vol. 5, No. 3, (2004), pp. 235-243.

(Continued)

*Primary Examiner* — Vanessa L. Ford
*Assistant Examiner* — Sandra E Dillahunt
(74) *Attorney, Agent, or Firm* — Annie J. Kock; Therese Marie Finan

(57) ABSTRACT

Provided is a technique that uses an established hepatocyte cell line in a method for evaluating an effect of a cytokine on a metabolic activity of a cytochrome P450 and in a method for evaluating a drug which interacts with a cytokine. The method for evaluating an effect of a cytokine on a metabolic activity of a cytochrome P450 includes: culturing an established hepatocyte cell line by using a culture chamber (10) including culture rooms (11), to thereby form spheroids (9); and evaluating the presence or absence of induction or attenuation of the cytochrome P450 after bringing a spheroid-shaped established hepatocyte cell line into contact with a test solution containing the cytokine in the culture chamber for one hour or more and less than 96 hours.

4 Claims, 22 Drawing Sheets

(56) References Cited

OTHER PUBLICATIONS

Dickmann, L.J., et al., "Effects of Interleukin-6 (IL-6) and an Anti-IL-6 Monoclonal Antibody on Drug-Metabolizing Enzymes in Human Hepatocyte Culture", Drug Metabolism and Disposition, vol. 39, No. 8, (2011), pp. 1415-1422.

Schmitt, C., et al., "Disease-Drug-Drug Interaction Involving Tocilizumab and Simvastatin in Patients with Rheumatoid Arthritis", Clinical Pharmacology & Therapeutics, vol. 89, No. 5, (May 2011), pp. 735-740.

Nagamori, S., "Ko Kino Hoji Hito Kan Saibo Kumikomigata Saibo Chip to Nano Sensor ni yoru Shin'yaku Kaihatsu ni Okeru Yakubutsu Dotai. Dokusei o Hyoka suru Shinki Bio Sensor no Kaihatsu", Heisei 18 Nendo Seisaku Soyaku Sogo Kenkyu Juten Kenkyu Hokokusho (II), (Jul. 31, 2007), (Total pp. 16).

Christensen, H., et al., "Immunological response as a source to variability in drug metabolism and transport", Frontiers in Pharmacology, vol. 3, Article 8, (Feb. 2012), pp. 1-10.

Ejiri, Y., et al., "Iyakuhin Kaihatsu no Tameno Shinki Hito Kan Saibo Baiyokei no Kochiku", Dai 16 Kai HAB Kenkyu Kiko Gakujutsu Nenkai Program Yoshishu, (May 22, 2009), (Total pp. 2).

Mimura, H., et al., "Micro Kukan Plate o Mochiite Baiyo shita Hito Kangan Yurai Saibo ni Okeru Enshosei Cytokine no Yakubutsu Dotai Kanren Idenshi Hatsugen eno Eikyo", The Pharmaceutical Society of Japan Dai 132 Nenkai Program, (Mar. 30, 2012), (Total pp. 7).

International Search Report dated Nov. 26, 2013 in PCT/JP2013/005770 Filed Sep. 27, 2013.

Combined Chinese Office Action and Search Report dated Jan. 4, 2016 in Patent Application No. 201380061684.X (with partial unedited computer generated English translation of First Notification of Reason for Refusal and English translation of categories of cited documents).

Extended European Search Report dated Mar. 4, 2016 in Patent Application 13840609.5.

Zhi-Guo Sheng, et al., "Application of in Vitro Three-Dimensional Cell Culture in Pharma-Toxicology Study" Chin J Pharmacol Toxicol, Oct. 31, 2007, 5 Pages (with English Abstract).

Jian Zhong Tong, et al., "Long-Term Culture of Adult Rat Hepatocyte Spheroids" Experimental Cell Research, vol. 200, No. 2, XP024791697, Jun. 1, 1992, pp. 326-332.

Edward T. Morgan, et al., "Anthony Y. H. Lu Commemorative Issue Physiological and Pathophysiological Regulation of Cytochrome P450" Drug Metabolism and Disposition, vol. 26, No. 12, XP055251908, Jan. 1, 1998, pp. 1232-1240.

Jukka Hakkola, et al., "Mechanisms of Down-Regulation of CYP2E1 Expression by Inflammatory Cytokines in Rat Hepatoma Cells" The Journal of Pharmacology and Experimental Therapeutics, vol. 304, No. 3, XP55251959, Mar. 1, 2003, pp. 1048-1054.

Ikada, "Surface modification of polymers for medical applications", Biomaterials 1994, 15(1) pp. 725-736.

\* cited by examiner

Fig. 17

| CYTOKINE | ANALYSIS METHOD | CYP | DETERMINATION AS TO PRESENCE OR ABSENCE OF CONCENTRATION DEPENDENCY | |
|---|---|---|---|---|
| | | | EXAMPLE | COMPARATIVE EXAMPLE |
| EGF | GENE ANALYSIS | CYP3A4 | PRESENT | NONE |
| HB-EGF | GENE ANALYSIS | CYP3A4 | PRESENT | NONE |
| IL-1β | GENE ANALYSIS | CYP3A4 | PRESENT | PRESENT |
| TNF-α | GENE ANALYSIS | CYP3A4 | NONE | NONE |
| | | CYP2C9 | NONE | NONE |
| IL-6 | GENE ANALYSIS | CYP3A4 | PRESENT | PRESENT |
| | WB | CYP3A4 | PRESENT | NONE |
| | ACTIVITY MEASUREMENT | CYP3A4 | PRESENT | NONE |

Fig. 18

| CYTOKINE | ANALYSIS METHOD | CYP | EXAMPLE | | | COMPARATIVE EXAMPLE | | |
|---|---|---|---|---|---|---|---|---|
| | | | EFFECT OF CYTOKINE | CONCENTRATION DEPENDENCY | OVERALL ASSESSMENT | EFFECT OF CYTOKINE | CONCENTRATION DEPENDENCY | OVERALL ASSESSMENT |
| EGF | GENE ANALYSIS | CYP3A4 | ATTENUATION | ATTENUATION | ATTENUATION | ATTENUATION | — | ATTENUATION |
| HB-EGF | GENE ANALYSIS | CYP3A4 | ATTENUATION | ATTENUATION | ATTENUATION | — | — | — |
| IL-1β | GENE ANALYSIS | CYP3A4 | ATTENUATION | ATTENUATION | ATTENUATION | — | ATTENUATION | ATTENUATION |
| TNF-α | GENE ANALYSIS | CYP3A4 | ATTENUATION | — | ATTENUATION | — | — | — |
| | | CYP2C9 | ATTENUATION | — | ATTENUATION | — | — | — |
| IL-6 | GENE ANALYSIS | CYP3A4 | ATTENUATION | ATTENUATION | ATTENUATION | — | ATTENUATION | ATTENUATION |
| | WB | CYP3A4 | ATTENUATION | ATTENUATION | ATTENUATION | — | — | — |
| | ACTIVITY MEASUREMENT | CYP3A4 | ATTENUATION | ATTENUATION | ATTENUATION | — | — | — |

METHOD FOR EVALUATING EFFECT OF CYTOKINE ON METABOLIC ACTIVITY OF CYTOCHROME P450, AND DRUG SCREENING METHOD

TECHNICAL FIELD

The present invention relates to a method for evaluating an interaction between a cytokine and a cytochrome P450, for example, a method for evaluating the induction and attenuation of a drug-metabolizing function of the cytochrome P450 due to the cytokine. The present invention also relates to a method for screening a drug which interacts with a cytokine.

BACKGROUND ART

In recent years, various studies of cytokines have been conducted.

For example, it has been disclosed that the blood level of interleukin in a patient suffering from inflammatory autoimmune disease is higher than that in a healthy human and the metabolic function of a cytochrome P450 in the patient is lower than that in a healthy human; and the metabolic function of CYP3A4 is reduced due to cytokines secreted into blood during inflammation, which makes it difficult to excrete drugs and results in serious side effects (Non Patent Literature 1). In a case where a pharmaceutical (D1) which undergoes the metabolism of the cytochrome P450 is administered to such a patient, a smaller dose of the drug than that for a healthy human is administered to the patient in anticipation of reduction in the metabolic function of the patient. When a drug (D2) (for example, a molecularly-targeted drug), which interacts with a cytokine and blocks interleukin receptors, is used together for the patient, the reduced metabolic function of the cytochrome P450 is restored and the metabolism of the pharmaceutical (D1) is promoted. As a result, according to a clinical study, the action of the pharmaceutical (D1) is attenuated (Non Patent Literature 2). Under such circumstances, the study of the interaction between the drug, such as molecularly-targeted drug, and the pharmaceutical, which undergoes the metabolism of the cytochrome P450, through cytokines has attracted attention.

An example of such techniques is animal testing. However, animal testing has a problem that a reaction in a living organism cannot be correctly predicted due to a species difference between humans and animals (Non Patent Literature 3). Additionally, an in vivo test, such as animal testing, provides a lower throughput performance than that of an in vivo system. Therefore, there is a problem that animal testing is not suitable for drug screening to evaluate a large number of compounds at the same time.

Under such circumstances, there has been a demand for an evaluation method using an in vivo test which can correctly predict a reaction in a living organism. Further, cytokines typified by interleukin have attracted attention as a drug discovery target. In recent years, there is a demand for an in vivo system for evaluating an interaction between drugs and cytokines.

CITATION LIST

Non Patent Literature

[Non Patent Literature 1] Kenneth W. Renton, "Cytochrome P450 Regulation and Drug Biotransformation During Inflammation and Infection", Current Drug Metabolism, May 2004, pp. 235-243

[Non Patent Literature 2] Leslie J. Dickmann, Sonal K. Patel, Dan A. Rock, Larry C. Wienkers, and J. Greg Slatter, "Effects of Interleukin-6 (IL-6) and an Anti-IL-6 Monoclonal Antibody on Drug-Metabolizing Enzymes in Human Hepatocyte Culture", DRUG METABOLISM AND DISPOSITION 39, 2011, pp. 1415-1422

[Non Patent Literature 3] C Schmitt, B Kuhn1, X Zhang, A J Kivitz3 and S Grange, "Disease-Drug-Drug Interaction Involving Tocilizumab and Simvastatin in Patients With Rheumatoid Arthritis", Clinical pharmacology &Therapeutics, VOLUME 89 NUMBER 5, May 2011, pp. 735-740

SUMMARY OF INVENTION

Technical Problem

As an in vivo test, Non Patent Literature 3 discloses a method using human primary hepatocytes. However, human primary hepatocytes have large lot-to-lot variations in the expression levels of pharmacokinetic genes and the inducibility thereof due to the donor gene polymorphism and environmental factors. In addition, the source of human primary hepatocytes is limited, and thus human primary hepatocytes are expensive and difficult to treat. Accordingly, there is a problem that it is difficult to evaluate a plurality of cytochromes P450 of cells of the same lot at once using various types of cytokines, or the evaluation cost is high.

On the other hand, an established hepatocyte cell line can be allowed to proliferate. Accordingly, if an established hepatocyte cell line of human origin can be used in a method for evaluating an effect of a cytokine on the metabolic activity of the cytochrome P450, it is expected that a reproducible result can be obtained at low cost. However, it is known that the functions of hepatocytes which are included in the metabolic functions of an established hepatocyte cell line are greatly lower than those of a primary hepatocyte. For example, in a case where an established hepatocyte cell line is cultured using a culture chamber with a flat bottom surface on which cells are cultured, the metabolic activity of the cytochrome P450 is equal to or less than a measurement limit value, which may make it difficult to analyze the metabolic activity. In such a case, even if the metabolic function can be detected using a control group in which no cytokines are added, it is extremely difficult to measure the amount of attenuation of the metabolic function when cytokines are added. To overcome such a problem, various types of three-dimensional cultures have been studied. However, the three-dimensional cultures have a problem that their operation is complicated, a special device is required, and the cost is high. Under such circumstances, a method for evaluating the effect of a cytokine on the metabolic activity of the cytochrome P450 by using an established hepatocyte cell line has not been developed.

The present inventors have found a technique that uses an established hepatocyte cell line in a method for evaluating an effect of a cytokine on the metabolic activity of the cytochrome P450 and in a method for screening a drug which interacts with a cytokine.

Solution to Problem

The present inventors have solved the above-mentioned problems by using a method for measuring a metabolic activity of a cytochrome P450 after bringing a spheroid-shaped established hepatocyte cell line into contact with a test solution containing a cytokine for one hour or more and less than 96 hours.

One aspect of a method for evaluating an effect of a cytokine on a metabolic activity of a cytochrome P450 according to the present invention is to evaluate the presence or absence of induction or attenuation of a metabolic function of the cytochrome P450 after bringing a spheroid-shaped established hepatocyte cell line into contact with a test solution containing the cytokine in a culture chamber for one hour or more and less than 96 hours. The present inventors have found that the metabolic function can be measured by forming a spheroid-shaped established hepatocyte cell line and bringing the spheroid-shaped established hepatocyte cell line into contact with a test solution for an appropriate time. This method enables the measurement and evaluation of the effect of the cytokine on the metabolic activity of the cytochrome P450.

In the one aspect of the method for evaluating the effect of the cytokine on the metabolic activity of the cytochrome P450 according to the present invention, it is preferable that an average value of diameters of spheroids formed from the established hepatocyte cell line be equal to or more than 50 μm and less than 200 μm, and it is also preferable that spheroids having a diameter within a half-width range account for 70% or more of all spheroids. The size of the diameter of each spheroid is within a predetermined range and a variation in the size of the diameter of each spheroid is reduced, thereby making it possible to improve the accuracy of determining the metabolic function.

Further, in the one aspect of the method for evaluating the effect of the cytokine on the metabolic activity of the cytochrome P450 according to the present invention, it is preferable that the test solution is a serum-free culture medium.

Additionally, it is preferable to use at least three types of test solutions, the at least three types of test solutions containing the cytokine at a concentration equal to a reference concentration, at a concentration that is 10 times higher than the reference concentration, and at a concentration that is 100 times higher than the reference concentration, respectively, the reference concentration being one of cytokine concentrations of the test solutions which are in a range from 0.1 times to 50 times higher than an average value of blood levels of cytokines in a healthy human. It is also preferable to use at least three types of test solutions, the at least three types of test solutions containing the cytokine at a concentration equal to a reference concentration, at a concentration that is 10 times higher than the reference concentration, and at a concentration that is 100 times higher than the reference concentration, respectively, the reference concentration being one of cytokine concentrations of the test solutions which are in a range from 0.1 times to 50 times higher than an average value of blood levels of the cytokine secreted from a patient with a disease.

In the one aspect of the method according to the present invention, it is preferable that a step of culturing the established hepatocyte cell line into a spheroid shape is carried out in a well and a step of bringing the spheroid-shaped established hepatocyte cell line into contact with the test solution containing the cytokine is carried out in the same well.

As the culture chamber, for example, one well of a culture plate including a plurality of wells is preferably used to carry out the steps of:

(1) forming a spheroid of the established hepatocyte cell line in a culture medium containing 10% serum in the one well;
(2) removing the culture medium from the one well;
(3) adding the test solution containing the cytokine to the one well; and
(4) bringing the test solution containing the cytokine into contact with the spheroid in the one well for one hour or more and less than 96 hours.

Moreover, the present inventors have solved the above-mentioned problems by using the method for measuring the metabolic activity of the cytochrome P450 after bringing the spheroid-shaped established hepatocyte cell line into contact with a test solution containing one of a cytokine and a drug.

A method for screening a drug which interacts with a cytokine according to another aspect of the present invention includes:

preparing a first test solution containing neither the cytokine nor the drug, a second test solution containing the cytokine and not containing the drug, and a third test solution containing both the cytokine and the drug;

bringing the first to third test solutions into contact with a spheroid-shaped established hepatocyte cell line in a culture chamber;

obtaining a first measurement value by measuring a function of a drug-metabolizing enzyme of a cytochrome P450 of the established hepatocyte cell line brought into contact with the first test solution, and obtaining second and third measurement values by measuring a function of a drug-metabolizing enzyme of the cytochrome P450 of the established hepatocyte cell line brought into contact with the second and third test solutions; and determining that the drug restores a drug-metabolizing function of the cytochrome P450, when the first measurement value is greater than the second measurement value and the second measurement value is smaller than the third measurement value.

The present inventors have found that this method makes it possible to use the established hepatocyte cell line in the method for screening a drug which interacts with a cytokine.

In the screening method according to the present invention, it is preferable that an average value of diameters of spheroids formed from the established hepatocyte cell line is equal to or more than 50 μm and less than 200 μm, and it is also preferable that spheroids have a diameter within a half-width range account for 70% or more of all spheroids. The size of the diameter of each spheroid is within a predetermined range and a variation in the size of the diameter of each spheroid is reduced, thereby making it possible to improve the accuracy of determining the metabolic function.

Further, in the screening method according to the present invention, it is preferable that a solvent for the test solution is a serum-free culture medium.

Additionally, it is preferable to determine that the drug-metabolizing function of the cytochrome P450 is restored, when the third measurement value is three times greater than the second measurement value.

Moreover, it is preferable that cytokine concentrations of the second and third test solutions are selected from among at least three concentrations of the cytokine at which a measurement value obtained by measuring a function of a drug-metabolizing enzyme of the cytochrome P450 by bringing the established hepatocyte cell line into contact with a solution which does not contain the drug is smaller than the first measurement value, the at least three concentrations being equal to a reference concentration, 10 times higher than the reference concentration, and 100 times higher than the reference concentration, respectively, the reference concentration being one of cytokine concentrations which are in a range from 0.1 times to 50 times higher than an average value of blood levels of cytokines in a healthy human. It is also preferable that cytokine concentrations of the second and third test solutions be selected from among at least three concentrations of the cytokine at which a measurement value obtained by measuring a function of a drug-metabolizing enzyme of the cytochrome P450 by bringing the established hepatocyte cell line into contact with a solution which does not contain the drug is smaller than the first measurement value, the at least three concentrations being equal to a reference concentration, 10 times higher than the reference concentration, and 100 times higher than the reference concentration, respectively, the reference concentration being one of cytokine concentrations which are in a range from 0.1 times to 50 times higher than a blood level of the cytokine secreted from a patient with a disease.

In the screening method according to the present invention, it is preferable that a step of culturing the established hepatocyte cell line into a spheroid shape and a step of bringing the spheroid-shaped established hepatocyte cell line into contact with the first to third test solutions be carried out in a well of a culture plate.

Advantageous Effects of Invention

According to the present invention, it is possible to use an established hepatocyte cell line in a method for evaluating an effect of a cytokine on a metabolic activity of a cytochrome P450 and in a method for screening a drug which interacts with a cytokine.

BRIEF DESCRIPTION OF DRAWINGS

FIG. 17 is a table showing results of determination of test results as to the concentration dependency of cytokines;

FIG. 18 is a table showing results of determination of test results based on a technique described in an evaluation process;

DESCRIPTION OF EMBODIMENTS

Figure 1:
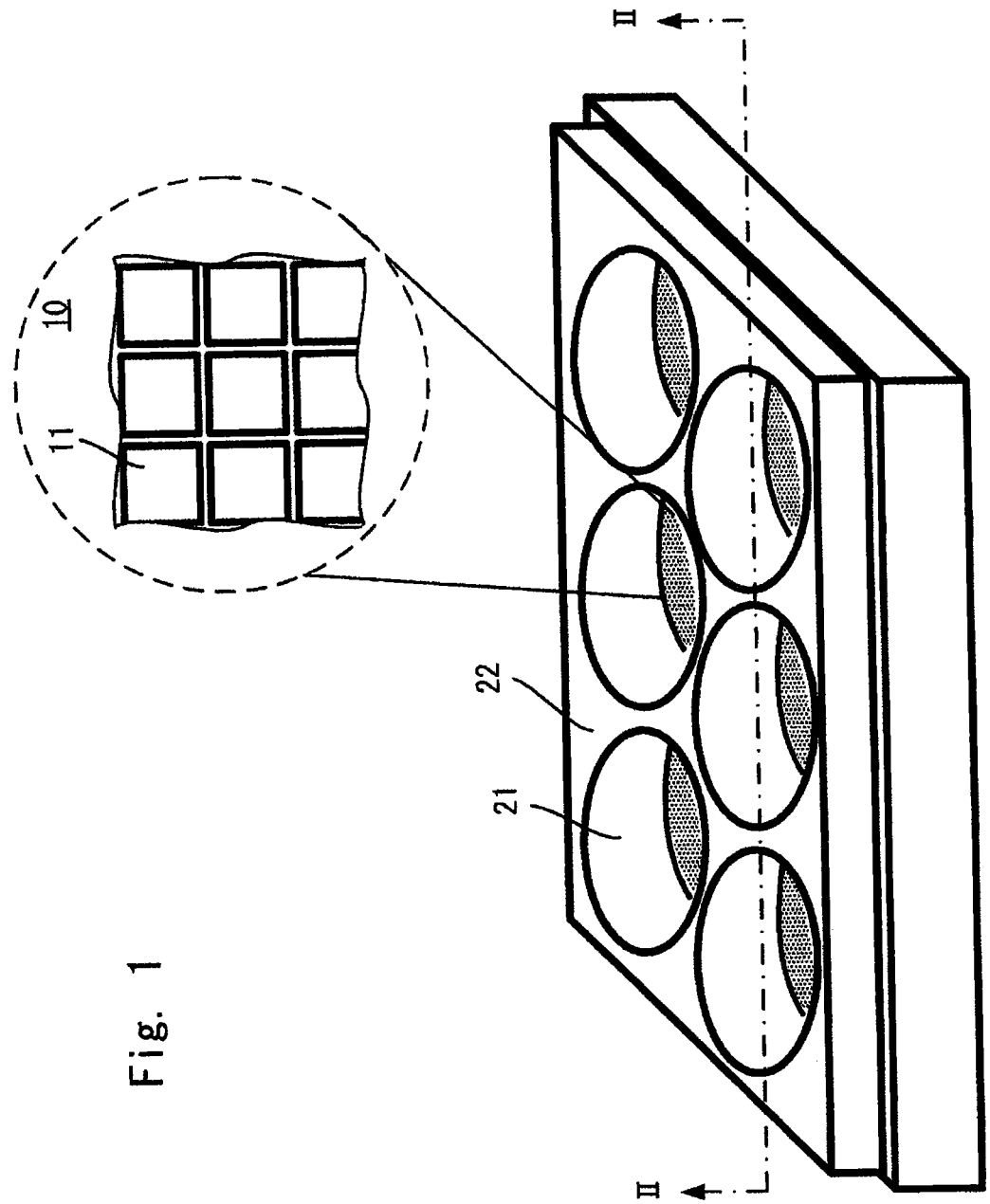
FIG. 1 is a view showing the overall structure of a culture plate used in an embodiment of the present invention.

Hereinafter, an embodiment of the present invention will be described with reference to the drawings. For clarity of explanation, the following description and the drawings are abbreviated and simplified as appropriate. The components having the same structure or function and corresponding parts in the drawings are denoted by the same reference numerals, and the description thereof is omitted.

The present inventors have solved the above-mentioned problems by using, as a method for evaluating an effect of a cytokine on a metabolic activity of a cytochrome P450 (the method is hereinafter referred to as "evaluation method" as appropriate), a technique of measuring the metabolic activity of the cytochrome P450 after bringing a spheroid-shaped established hepatocyte cell line into contact with a test solution containing the cytokine for one hour or more and less than 96 hours, and evaluating the metabolic activity of the cytochrome P450 due to the cytokine. More specifically, the evaluation method includes: culturing an established hepatocyte cell line of human origin to form a spheroid; bringing the spheroid-shaped established hepatocyte cell line into contact with a test solution containing the cytokine in a culture chamber for one hour or more and less than 96 hours; and measuring the value of the cytochrome P450 of the established hepatocyte cell line. Based on the measurement result, the evaluation of the metabolic activity of the cytochrome P450, in other words, the evaluation of the presence or absence of induction or attenuation of the metabolic activity of the cytochrome P450 due to the cytokine is made as follows. That is, when the value of the cytochrome P450 increases, it is determined that "the cytokine induces the metabolic function of the cytochrome P450", and when the value of the cytochrome P450 decreases, it is determined that "the cytokine attenuates the metabolic function of the cytochrome P450".

The present inventors have also found that a method for screening a drug which interacts with a cytokine (the method is hereinafter referred to as "screening method" as appropriate) can be implemented by the following procedure. Three types of test solutions, that is, (A) a first test solution containing neither the cytokine nor the drug, (B) a second test solution containing the cytokine but not containing the drug, and (C) a third test solution containing both the cytokine and the drug, are prepared. Further, an established hepatocyte cell line is cultured using a culture chamber including culture rooms, to thereby form a spheroid. The first to third test solutions are brought into contact with the spheroid-shaped established hepatocyte cell line. A first measurement value is obtained by measuring a function of a drug-metabolizing enzyme of the cytochrome P450 of the established hepatocyte cell line brought into contact with the first test solution. Similarly, second and third measurement values are obtained by measuring a function of a drug-metabolizing enzyme of the cytochrome P450 of the established hepatocyte cell line brought into contact with the second and third test solutions. As a result of the measurement, when the first measurement value is greater than the second measurement value and the second measurement value is smaller than the third measurement value, it is determined that the drug restores the drug-metabolizing function of the cytochrome P450.

The term "cytokine" is a general term for protein factors which are released from cells and mediate an interaction between various cells. The cytokine is a substance that plays the role of, for example, regulating the immune system, evoking an inflammatory response, antitumor action, cell proliferation, differentiation, and suppression, which are necessary for maintenance of homeostasis in a living organism. In one embodiment, especially, attention is focused on a cytokine that causes a variation (induction, attenuation) in liver function due to the presence of the cytokine. Examples of the cytokine include a growth factor, an interferon, and a tumor necrosis factor.

The term "spheroid" refers to a cell mass formed as a result of aggregation of a number of cells in a three-dimensional state.

The term "cytochrome P450 (CYP)" refers to an enzyme that plays the role of xenobiotic (drug) metabolism and is present in almost all living organisms including bacteria, plants, and mammals. In the case of animals, the cytochrome P450 (CYP) is present mainly in the liver.

The term "a drug which interacts with a cytokine" (hereinafter referred to also as "drug" as appropriate) refers to a drug which interacts with a cytokine, if there is any cytokine. In particular, the drug causes a variation in the metabolic function of the cytochrome P450 due to an interaction with the cytokine. Examples of the drug include biotechnology-based pharmaceuticals using proteins, genes, and the like in the body, and low-molecular pharmaceuticals.

In the following description, unless otherwise specified, the case of "a range from a value A to a value B" indicates "equal to or greater than the value A and equal to or less than the value B".

The term "value of cytochrome P450" refers not to a value representing the total amount of the cytochrome P450, but to a value representing the metabolic function of the cytochrome P450. Examples of the value of the cytochrome P450 include a value of metabolic activity, a gene expression level, and an amount of protein.

As for an evaluation method and a screening method according to one embodiment, a culture chamber for culturing an established hepatocyte cell line will now be described below. Next, a culture and evaluation method in the process from culture of an established hepatocyte cell line to evaluation of the established hepatocyte cell line will be described.

1. Culture Chamber

Outline of Culture Chamber

Figure 2A:
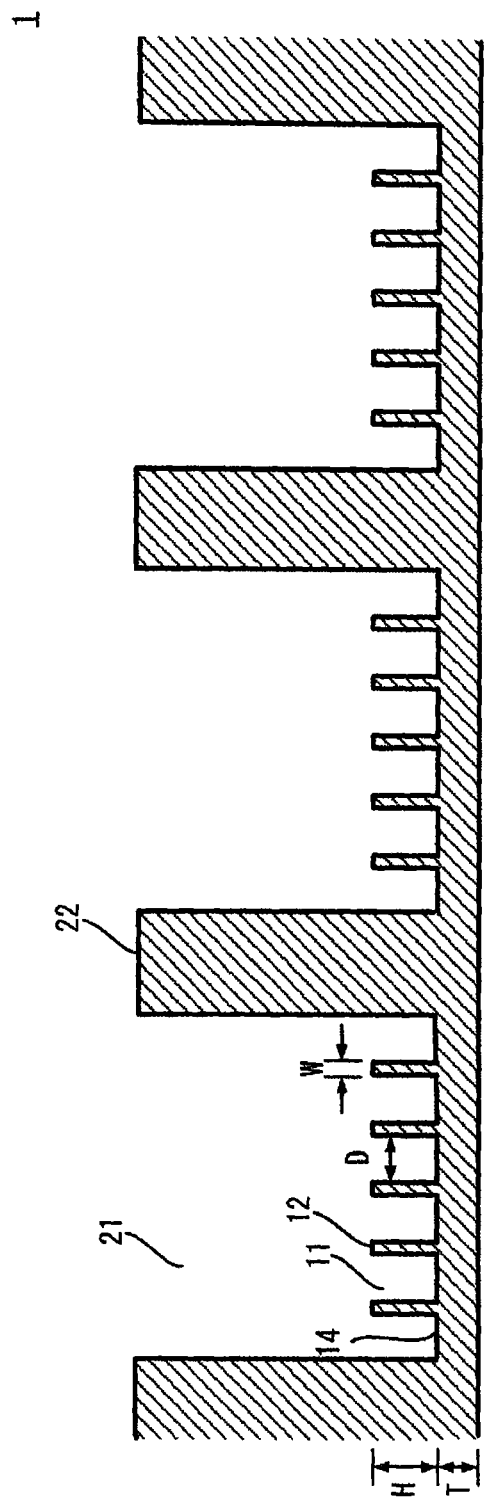
FIG. 2A is a sectional view of the culture plate taken along the line II-II of FIG. 1.
Figure 2B:
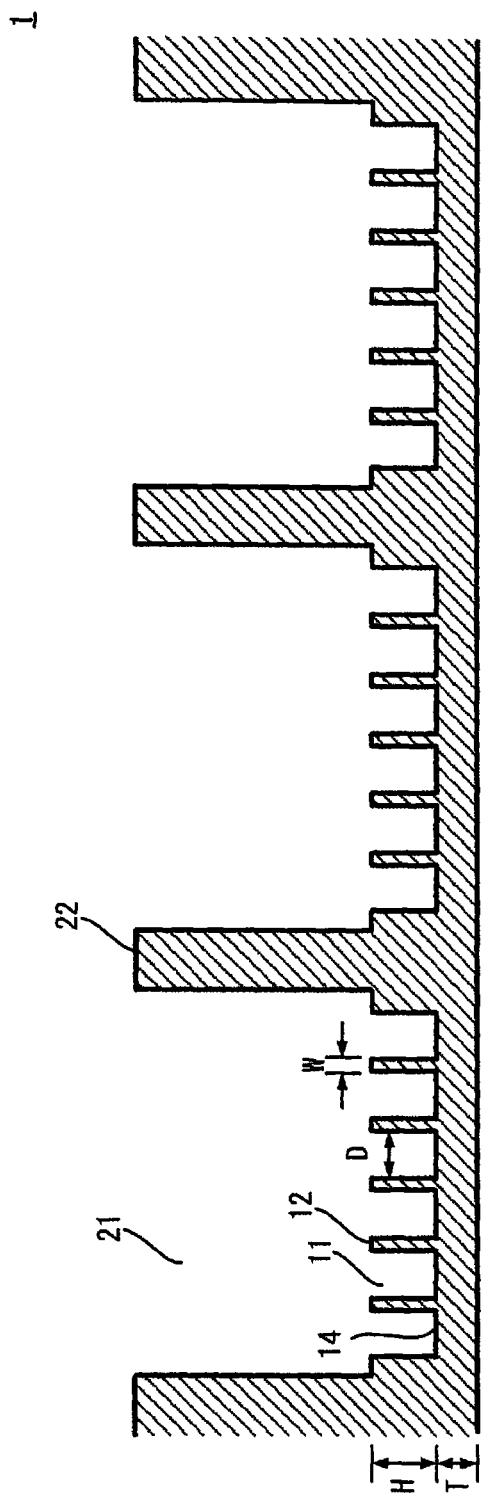
FIG. 2B is another sectional view of the culture plate taken along the line II-II of FIG. 1.

FIG. 1 is a view showing the overall structure of a culture plate used in an embodiment of the present invention. FIG. 2A is a sectional view of the culture plate taken along the line II-II of FIG. 1. FIG. 2B is another sectional view of the culture plate. A culture plate 1 includes a plurality of wells 21. In the plurality of wells 21, the adjacent wells 21 are partitioned by partitions 22. A culture chamber 10 is formed in each of the plurality of wells 21.

Figure 3:
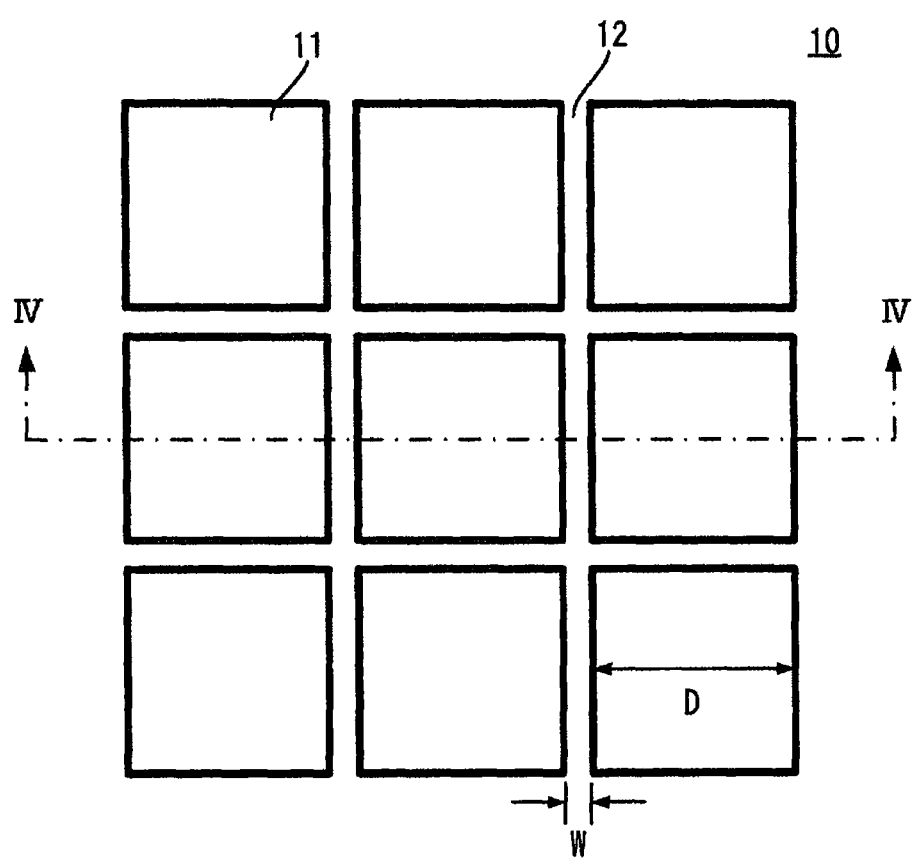
FIG. 3 is a diagram showing the overall structure of a culture chamber used in an embodiment of the present invention.
Figure 4:
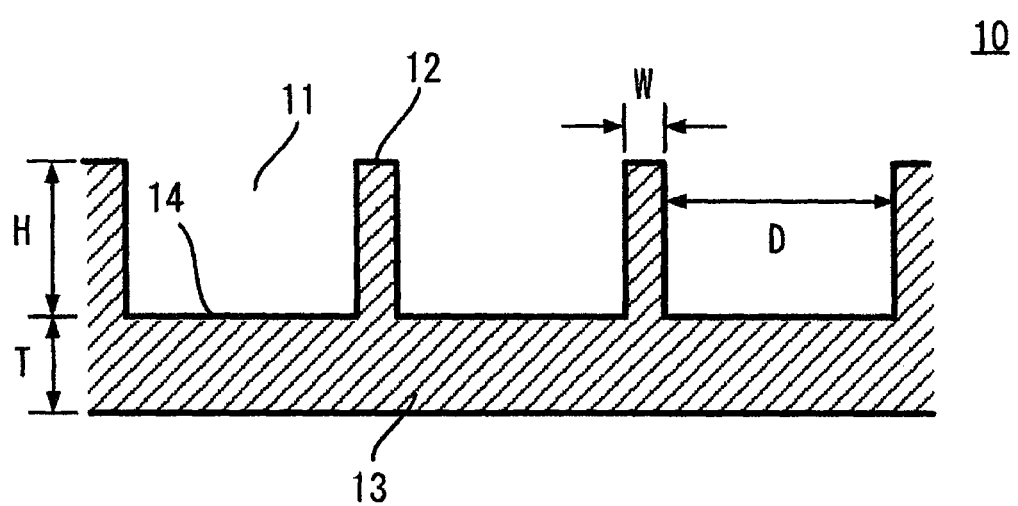
FIG. 4 is a sectional view of the culture chamber taken along the line IV-IV of FIG. 3.

FIG. 3 shows a structural example of the culture chamber used in an embodiment of the present invention. FIG. 4 is a sectional view of the culture chamber taken along the line Iv-Iv of FIG. 3.

The culture chamber 10 includes culture rooms 11, walls 12, and a bottom portion 13.

Each culture room 11 is a region partitioned by the walls 12 and the bottom portion 13, and serves as a three-dimensional space region (culture region) in which cells are cultured. Each culture room 11 is also referred to simply as a "room" or "micro-room".

Each wall 12 is a partition wall that partitions the culture rooms 11, and is also referred to as a convex portion that forms a concave-convex pattern in the culture chamber 10. When some culture rooms 11 are adjacent to the partitions 22, the walls 12 may be identical with a part of the wall surface of the partitions 22 as shown in FIG. 2A. Alternatively, as shown in FIG. 2B, some walls 12 may be disposed so as to be adjacent to the wall surface of the corresponding partition 22.

The bottom portion 13 functions as a substrate of the culture chamber 10, and the surface on which the culture rooms 11 are disposed serves as a part of the culture region (culture surface). The bottom portion 13 is the same region as the bottom portion of each well 21 formed in the culture plate 1, and the bottom portion of each well 21 is used. The bottom portion 13 forms the bottom of each culture room 11. In the bottom portion 13, a surface that is a part of surfaces forming each culture room 11 and corresponds to the bottom portion of the culture region is also referred to as "bottom culture surface 14".

FIGS. 3 and 4 show an equivalent diameter D, a height (depth) H, a width (thickness) W of each wall 12, and a thickness T of the bottom portion 13 of each culture room 11 formed in the culture chamber 10. FIGS. 3 and 4 illustrate a case where the bottom portion 13 is formed integrally with each wall 12.

The term "equivalent diameter D" refers to the diameter of a circle inscribed in each culture room 11. More specifically, the term "equivalent diameter D" refers to the diameter of a circle inscribed in the shape of the surface parallel to the bottom portion 13 of each culture room 11 (the shape of the surface), or the shape of the surface that is perpendicular to the direction of the height H of each culture room 11. When the shape of the surface of each culture room 11 varies depending on the height H, a maximum value of the space region in which an established hepatocyte cell line is cultured is used as the equivalent diameter of the equivalent diameter.

The term "height H" refers to the length from the bottom (bottom culture surface 14) of each culture room 11 to an upper surface of each wall 12, and also refers to the depth of each culture room 11. When the bottom culture surface 14 is a flat surface, the height H is the same as the height of each wall 12.

The term "width W" of each wall 12 refers to the thickness of each wall 12, and also refers to the distance between the adjacent culture rooms 11.

In the culture chamber 10 (in other words, in each well 21), the plurality of culture rooms 11 are disposed in an array as shown in FIG. 3. The number and the size of the culture rooms 11 included in the culture chamber 10 depend on the number of the wells 21 (the size of the wells 21), which are formed in the culture plate 1, and on the size of the culture rooms 11 and the walls 12. Specifically, the number of the culture rooms 11 decreases as the number of the wells 21 increases. When the wells 21 have the same size, the number of the culture rooms 11 in each well 21 decreases as the equivalent diameter D or the width W increases. FIGS. 1 to 4 are schematic views showing a smaller number of the culture rooms 11 for ease of explanation of the structure. That is, the number of the culture rooms 11 is different from the actual number of the culture rooms 11 included in the culture chamber 10. Additionally, FIGS. 3 and 4 show nine culture rooms 11 for convenience of explanation. The number of culture rooms may be different from the actual number of the culture rooms 11 included in the culture chamber 10 (each well 21).

The present inventors have found that spheroids having a uniform diameter of an established hepatocyte cell line can be cultured by culturing an established hepatocyte cell line in each culture room 11 by using the culture chamber 10 which includes a plurality of culture rooms 11 each having the equivalent diameter D that is 1 to 5 times the diameter of a desired spheroid and having the height H that is 0.3 to 5 times the equivalent diameter D, and in which the water contact angle of the culture room surface is equal to or less than 45 degrees. Consequently, the size of each spheroid to be cultured can be controlled by selecting the size of the culture rooms 11, which are disposed in the culture chamber 10, depending on the size of a desired spheroid. In one embodiment, an established hepatocyte cell line of human origin is cultured as the established hepatocyte cell line, to thereby form a spheroid. This embodiment will be described in detail below.

Referring to FIGS. 1 to 4, the size, shape, and the like of the micro-order culture rooms 11 for forming a desired spheroid, and the characteristics of the culture surface will be described.

Size, Shape, and the Like of Culture Rooms

Regarding the equivalent diameter D of each culture room 11, it is necessary to consider that the diameter of each spheroid increases as the cells proliferate. In this case, it is important to secure the culture rooms 11 in which the spheroids are prevented from being brought into contact with the cells in the adjacent culture rooms 11. Accordingly, the equivalent diameter D of each culture room 11 is preferably in a range from 1 to 5 times the diameter of a desired spheroid, and more preferably, in a range from 1.2 to 4 times the diameter of a desired spheroid.

For example, in order to form a spheroid of an established hepatocyte cell line having a diameter of 100 µm, the culture chamber 10 having the following structure is used. That is, the equivalent diameter D of the culture chamber 10 is in a range from 1 to 5 times the diameter of a desired spheroid, i.e., in a range from 100 µm to 500 µm, and the culture chamber 10 includes the bottom portion 13 on which the culture rooms in which the value obtained by dividing the height H by the equivalent diameter D is in a range from 0.3 to 2 are regularly disposed.

For example, a study of a case where a cancer cell, which is one type of established hepatocyte cell lines, will be described.

When cells are allowed to proliferate and maintained by increasing the cell adhesion properties with respect to the surface of each culture room 11 for established hepatocyte cell lines, the cells sufficiently adhere to the bottom surface, which prevents the cells from being removed upon replacement of culture medium. Accordingly, since there is no need to secure such a deep space as each culture room 11 having the equivalent diameter D in the range from 1 to 5 times the diameter of a desired spheroid and having the height H in the range from 0.3 to 2 times the equivalent diameter D as in this embodiment, the cells are not cultured in such a room.

On the other hand, in one embodiment, the cell adhesion properties are suppressed as described later. Therefore, it is necessary to design an optimum height H to make it possible to supply amino acid, oxygen, and the like and prevent the spheroids from being removed. As a result of studying the preferred height H and equivalent diameter D to form a spheroid in a preferred range as described in paragraph 0018, the equivalent diameter D is preferably in a range from 100 µm to 200 µm and the height H is preferably in a range from 50 µm to 100 µm so as to prevent the spheroids from being excessively increased in size due to cell proliferation. To sufficiently supply nutrients, such as amino acid, to the bottom of each culture room 11 and to prevent accumulation of waste products, the height of each culture room 11 is preferably low as much as possible, unless the spheroids are removed during replacement of culture medium or replacement of test solution. Specifically, the present inventors have found that the value obtained by driving the height H of each culture room 11 by the equivalent diameter D is preferably in a range from 0.3 to 2, and more preferably, in a range from 0.5 to 1.

In one embodiment, to spread or transport a test solution to a central portion of a spheroid, the diameter of the largest spheroid is preferably less than a diameter of 200 µm, and more preferably, equal to or less than 150 µm. Additionally, to maximize the interaction between cells, the diameter of each spheroid is preferably equal to or larger than 50 µm, and more preferably, in a range from 60 µm to 150 µm. The term "interaction between cells" refers to an interaction between a test substance (for example, a cytokine) and a cytochrome P450.

The width W of each wall 12 corresponds to the thickness of each wall 12 that partitions the adjacent culture rooms 11. Accordingly, to prevent the cells from proliferating on an upper surface of each wall 12 and to allow the cells to easily enter the culture rooms 11, it is preferable to set the width W of each wall 12 in a range from 2 µm to 50 µm. Preferably, the width W is equal to or smaller than the size of one cell body, that is, in a range from 5 µm to 30 µm, and more preferably, in a range from 5 to 10 µm. From a similar point of view, an angle θ formed between an upper surface of each wall 12 and a side surface of each culture room 11 is preferably in a range from 90 degrees to 135 degrees, and more preferably, in a range from 90 degrees to 120 degrees.

Figure 5A:
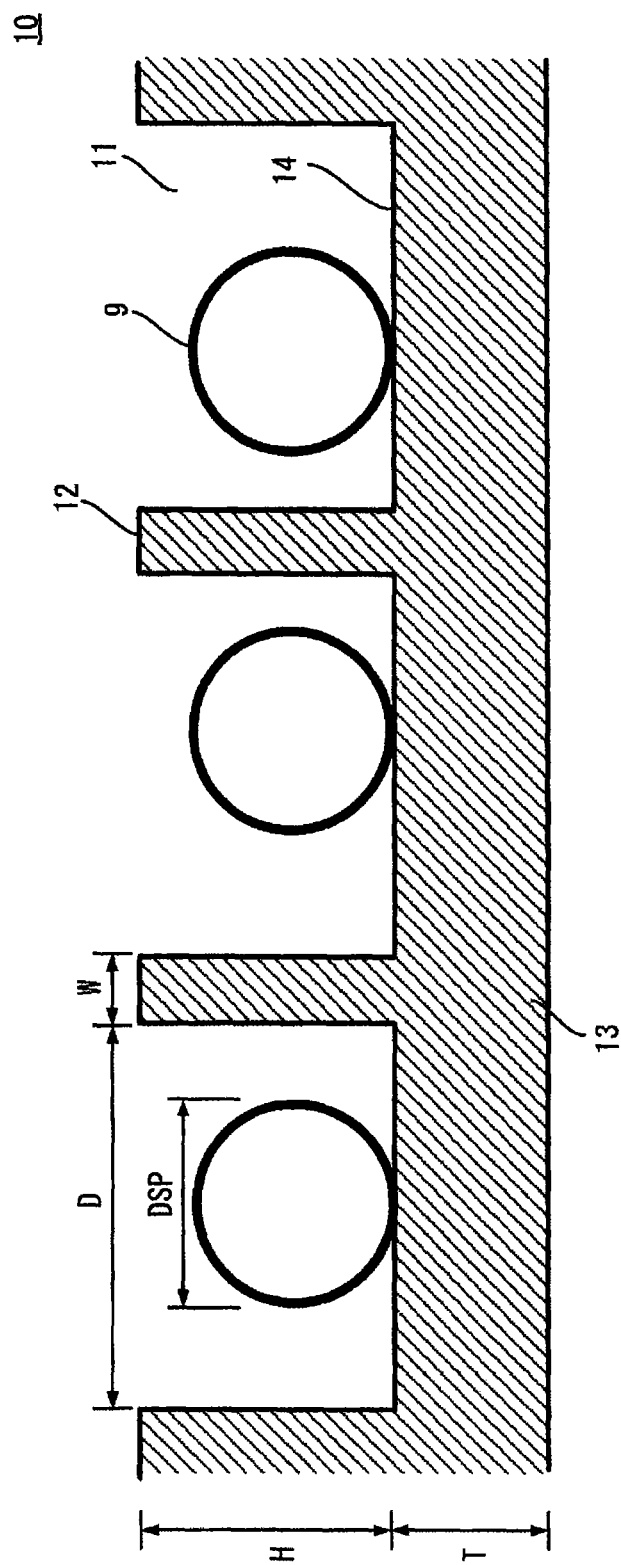
FIG. 5A is a schematic view showing a state in which spheroids cultured in respective culture rooms.

FIG. 5A is a schematic view showing a state in which spheroids are cultured in the respective culture rooms 11. In FIG. 5A, the sectional view of FIG. 4 is used and spheroids 9 are each indicated by "circle". The spheroids 9 are calculated in the respective culture rooms 11.

In the case of culturing spheroids in the culture plate 1 shown in FIG. 1, setting of culture conditions, replacement of culture medium, and the like are carried out for each well 21. Accordingly, since a plurality of culture rooms 11 are formed in each well 21, a plurality of spheroids can be cultured under the same conditions in each well 21. Additionally, since spheroids can be cultured using a well plate, conventionally used devices and the like for cell culture can be used.

Assuming that a diameter DSP of each spheroid 9 is represented as a value dsp (dsp represents a positive value), the equivalent diameter D of each culture room 11 is preferably in a range from the value dsp to a value that is five times the value dsp ($dsp \leq D \leq 5dsp$). Further, the height H of each culture room 11 is preferably in a range from 0.3 times to 25 times (5×5) higher than the value dsp ($0.3dsp \leq H \leq 25dsp$).

Figure 5B:
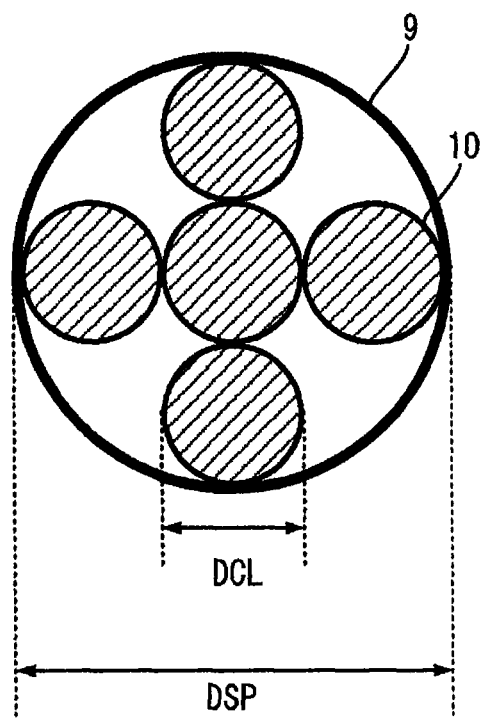
FIG. 5B is a schematic view illustrating an example of a preferred size of a spheroid cultured in a culture room.

FIG. 5B is a schematic view showing an example of a preferred size of each spheroid cultured in the culture rooms. FIG. 5B is a schematic view showing an end face of a cut section taken along the equivalent diameter D of the spheroid 9. As described above, the average of the diameters of the spheroids is preferably equal to or larger than 0 μm and less than 200 μm, and more preferably, in the range from 60 μm to 150 μm. FIG. 5B illustrates a state in which the end face of the cut section of the spheroid 9 is formed of five cells 8. For example, in the case of forming the spheroid 9 having the diameter DSP of 60 μm and including the cells 8 each having a diameter DCL of 20 μm, three cells 8 are aligned, for example, to thereby form the spheroid 9. Similarly, in the case of forming the spheroid 9 having the diameter DSP of 150 μm, five cells 8 are aligned, for example, to thereby form the spheroid 9. FIG. 5B schematically shows a state in which the cells 8 are aligned, for ease of explanation. However, the cells 8 are not necessarily aligned.

In addition, it is preferable that spheroids which are formed in one test region (one well, one petri dish) and have a diameter within a half-width range account for 70% or more of all spheroids. In other words, it is preferable that the spheroids have a uniform diameter. The reason for this is as follows. As it is known that the value of metabolic activity varies depending on the size of each spheroid, if there are various spheroids with different diameters, it is difficult to obtain highly accurate results. It is also known that the metabolic function of a small spheroid (50 μm or less) is extremely low. Accordingly, if a number of such spheroids are included, a value for evaluating cytokines that attenuate the metabolic function is equal to or less than a measurement limit value, which may make it difficult to determine the presence or absence of attenuation of the metabolic function.

The term "half-width range" refers to a number N2 which is the number of spheroids included in spheroids having a total number NT present in one test region. Considering the correlation between the size of the diameter of each spheroid and the number of existing spheroids, the number N2 is the number of spheroids being present in a range from a minimum diameter D2 to a maximum diameter D3 among a plurality of diameters corresponding to half of a number N1 (N1/2). The number N1 is the largest number of existing spheroids included in spheroids having the total number NT present in the one test region and a diameter D1. To form the spheroids with a uniform size, it is preferable that the number N2 of spheroids account for 70% or more of the total number NT of spheroids, and it is more preferable that the ratio of the number N2 of spheroids to the total number NT spheroids is higher.

Figure 6A:
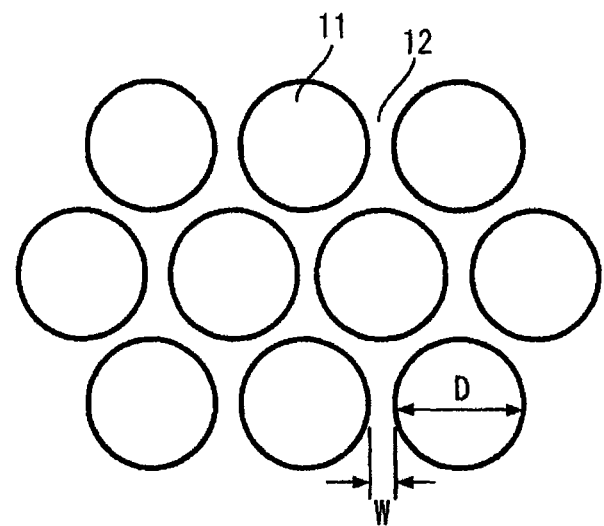
FIG. 6A is a diagram showing another example of the shape of each culture room.
Figure 6B:
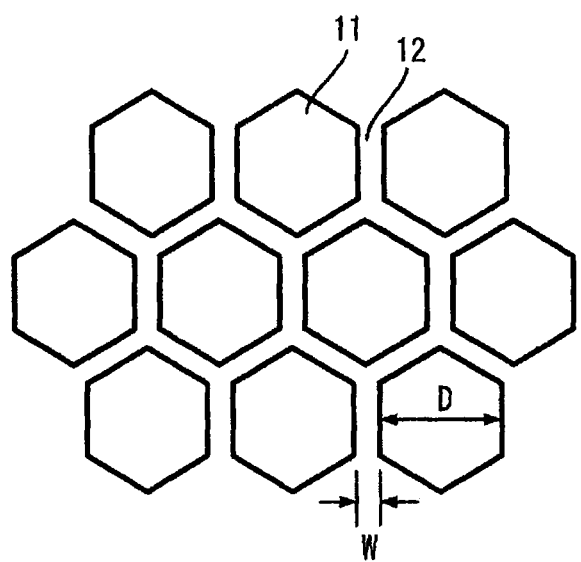
FIG. 6B is a diagram showing still another example of the shape of each culture room.

The shape (the shape of the surface) of each culture room 11, or the shape of the surface parallel to the bottom portion 13, is not limited to the shape shown in FIG. 3. For example, other shapes (an ellipse, a rhomboid etc.) as shown in FIGS. 6A to 6B may be used. To form spheroids having a uniform diameter at a higher density, it is preferable that the shape (the shape of the surface) of each culture room 11 has a symmetrical structure.

Figure 7A:
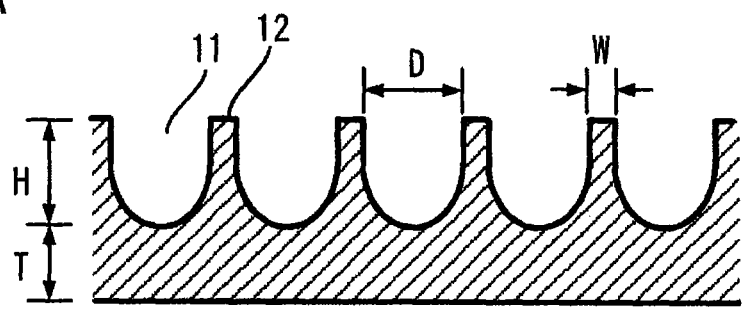
FIG. 7A is a sectional view showing another example of the shape of a side surface of each culture room.
Figure 7B:
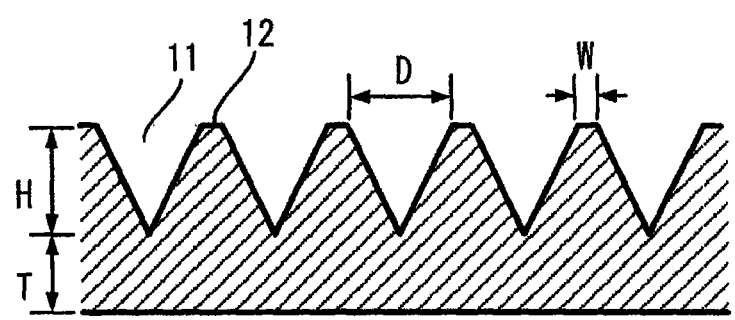
FIG. 7B is a sectional view showing still another example of the shape of a side surface of each culture room.
Figure 7C:
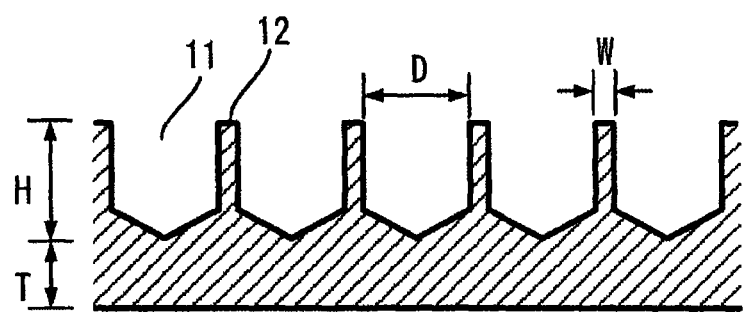
FIG. 7C is a sectional view showing still another example of the shape of a side surface of each culture room.

The shape of the side surface of each culture room 11 is not limited to the shape shown in FIG. 4. For example, shapes as shown in FIGS. 7A to 7C may be used.

A material for forming the culture chamber 10 is selected from the group consisting of acrylic resin, polylactic acid, polyglycolic acid, styrene resin, acrylic-styrene copolymer resin, polycarbonate resin, polyester resin, polyvinyl alcohol resin, ethylene-vinylalcohol copolymer resin, thermoplastic elastomer, vinyl chloride resin, and silicon resin, or a combination thereof.

In terms of observation performance, the thickness T of the bottom portion 13 of the culture chamber 10 is preferably 1 mm or less. However, the thickness may be 1 mm or more, as long as the thickness has no adverse effect on the observation with a microscope, and thus the thickness T of the bottom portion 13 is not limited. By securing the observation performance of the bottom portion 13 of the culture chamber, the cultured spheroids can be observed by using the culture plate without any change. Securing the observation performance of the culture chamber enables a fluorescent staining observation by immunohistology or in-situ method using reporter genes such as an in-situ method using reporter genes Green Fluorescent Protein (GFP), by using the culture chamber without any change.

Characteristics of Culture Surface

Next, characteristics of the culture surface on which cells are cultured, i.e., characteristics of the walls 12 surrounding the culture rooms 11 and the bottom culture surface 14, especially, a hydrophilic treatment will be described. At the culture surface, a culture medium is injected into each culture room 11. Further, in the case of using a coating solution, the culture surface cannot be covered until the solution is injected into each culture room 11. For this reason, the water contact angle is preferably set to 45 degrees or less, and more preferably, in a range from 0 to 20 degrees. Further, the value of the water contact angle is determined based on values obtained by preparing and measuring a flat plate with no concave-convex pattern of the culture rooms 11 and the walls 12 under the same conditions as those for the culture chamber 10.

As for the surface in which the culture rooms 11 are disposed in an array, in the case where the surface has a high hydrophobic property and a water contact angle of more than 45 degrees, that is, the surface has low wettability, when a culture medium or coating solution is added, air bubbles are liable to be trapped in each room, which may result in generation of a room in which cells cannot be cultured. Accordingly, it is necessary to perform a hydrophilic treatment so that the water contact angle becomes 45 degrees or less. Examples of the hydrophilic treatment method include a method of depositing $SiO_2$ and a method of performing a plasma treatment.

In addition, it is preferable to suppress the cell adhesion properties so as to effectively form spheroids in the culture chamber 10. The cell adhesion properties can be suppressed by using the surface having a water contact angle of 45 degrees or less, preferably 40 degrees or less, and more preferably 20 degrees or less. The relationship between the suppression of cell adhesion properties and the water contact angle is disclosed in, for example, "Surface modification of polymers for medical applications", written by Y Ikada, Biomaterials 1994, vol. 15 No. 10, pp. 725-736. Examples of a method for setting the water contact angle to 45 degrees or less includes a method of depositing glass on the culture bottom surface 14, and a method of forming a functional group on the surface by using a plasma treatment method. A functional group is formed on the surface by, for example, a plasma treatment.

Further, when the water contact angle is set to 45 degrees or less, cell adhesion properties are further suppressed by coating a substance for suppressing cell adhesion properties, thereby effectively forming spheroids. For example, after a plasma treatment is carried out and the water contact angle is set to 45 degrees or less, a phospholipid-polymer complex or poly(2-hydroxyethyl methacrylate) may be coated.

2. A Method for Culturing and Evaluating an Established Hepatocyte Cell Line and a Drug Screening Method Next, a method for culturing an established hepatocyte cell line and evaluating an effect of a cytokine on the metabolic activity of a cytochrome P450 will be described.

Outline of the Culture and Evaluation Method and the Drug Screening Method

In the process from culture of an established hepatocyte cell line to evaluation of the established hepatocyte cell line according to an embodiment, for example, the following processes (A) to (F) are carried out.

(A) A process of culturing an established hepatocyte cell line of human origin to form a spheroid (spheroid formation process).

(B) A process of removing a culture medium from a single well 21 (culture medium removing process).

(C) A process of adding, to the well 21, a test solution containing the cytokine, or a control solution (test solution addition process).

(D) A process of bringing the test solution containing the cytokine into contact with the spheroid-shaped established hepatocyte cell line in the well 21 for one hour or more or less than 96 hours (contact process).

(E) A process of analyzing the metabolic function of the cytochrome P450 (analysis process).

(F) A process of evaluating the analysis result (evaluation process).

Outline of Screening Method

In the process from culture of an established hepatocyte cell line to determination thereof according to an embodiment, for example, the following processes (A') to (F') are carried out.

(A') A process of culturing an established hepatocyte cell line of human origin to form a spheroid (spheroid formation process).

(B') A process of removing a culture medium from a single well 21 (culture medium removing process).

(C') A process of adding first to third test solutions to the well 21 (test solution addition process).

(D') A process of bringing a test solution containing the cytokine into contact with the spheroid-shaped established hepatocyte cell line in the well 21 for one hour or more and less than 96 hours (contact process).

(E') A process of analyzing (measuring) the metabolic function of the cytochrome P450 (analysis process).

(F') A process of determining the analysis result (determination process).

In this case, the first test solution is a solution containing neither the cytokine nor the drug (cytokine-free and drug-free). The second test solution is a solution containing the cytokine but not containing the drug (cytokine-containing and drug-free). The third test solution is a solution containing both the cytokine and the drug (cytokine-containing and drug-containing). The first to third test solutions are brought into contact with the spheroid-shaped established hepatocyte cell line, and the results obtained by measuring the metabolic function of the cytochrome P450 are used as first to third measurement values.

In the evaluation method according to an embodiment, a culture plate including a plurality of wells is preferably used in terms of operability. Especially, the spheroid formation process (Processes A and A') in which an established hepatocyte cell line is cultured into a spheroid shape and the contact process (Processes D and D') in which the test solutions containing the cytokine are brought into contact with the cultured cells for a predetermined time are preferably carried out in the same well. Accordingly, in one embodiment, the plurality of wells 21 of the culture plate 1 shown in FIG. 1 are used, and the processes from the spheroid formation process to the contact process are continuously carried out in each of the plurality of wells 21. In other words, in the process from culture of an established hepatocyte cell line to evaluation of the established hepatocyte cell line in one well, the cells are not moved to another well 21 in the middle of the processes.

Unless otherwise specified, Processes A' to D' are represented as Processes A to D in the following description.

Process A: Spheroid Formation Process

In the spheroid formation process of Process A, the above-described culture chamber 10 is used to culture an established hepatocyte cell line of human origin in a culture medium containing 10% serum, to thereby form a spheroid of a desired size.

At least a part of the spheroid thus formed adheres to the walls 12 or the bottom culture surface 14.

A method for obtaining the spheroid-shaped established hepatocyte cell line is not particularly limited to, for example, roller bottle culture, spinner flask culture, and hanging-drop culture. However, devices to be used in these methods are changed depending on the culture method, which causes the necessity of carrying out the spheroid formation process and the contact process in different chambers. The present inventors have found that the use of the wells 21 each having the above-described culture chamber 10 formed therein makes it possible to carry out the spheroid formation process and the contact process in the same chamber. This results in simplifying the operation and making it possible to bring the cells into contact with the cytokine without moving the formed spheroids. Especially, an automatic culture device can be used in pharmaceutical screening for evaluating a number of compounds at once. Additionally, damage to the cells and contamination thereof can be prevented.

While the preferred size of the culture chamber 10 to form a spheroid has been described above, it has been found that when the processes from the spheroid formation process to the contact process are carried out, the following size of the culture chamber 10 is especially preferable.

In the culture chamber 10, at least two culture rooms 11 which have the equivalent diameter D in a range from 100 µm to 1000 µm and in which the value obtained by dividing the height H by the equivalent diameter D is in a range from 0.3 to 2 are preferably disposed. Additionally, it is preferable that the width W of each wall 12 that partitions the culture rooms 11 is in a range from 2 μm to 50 μm. The use of the culture chamber 10 having a structure as described above makes it possible to easily obtain spheroids having a uniform diameter.

In order to effectively form spheroids in the culture chamber 10 including the culture rooms 11, it is preferable to suppress the cell adhesion. On the other hand, for the purpose of preventing the spheroids from being removed from the culture rooms during replacement of culture medium or replacement of test solution, it is preferable that a part of the spheroids adhere to the culture surface (the surface of each wall 12 or the bottom culture surface 14). Accordingly, a mixture of a polymer that inhibits adhesion of cells to the culture surface and a polymer that promotes adhesion of cells to the culture surface may be coated on the culture surface. The polymer that inhibits adhesion of cells to the culture surface is a polymer selected from the group consisting of a hydrophilic polymer chain, phospholipid, a phospholipid-polymer complex, poly(2-hydroxyethyl methacrylate) (PHEMA), polyvinyl alcohol, agarose, chitosan, polyethyleneglycol, and albumin, which inhibit the cell adhesion, or a combination thereof. The polymer that promotes the cell adhesion properties is a polymer selected from the group consisting of poly-L-lysine, poly-D-lysine, collagen, laminin, and fibronectin, or a combination thereof. Examples of the coating solution include a mixture of phospholipid, 2-methacryloyloxyethyl phosphorylcholine (MPC) polymer, which is a phospholipid-polymer complex, and a poly-L-lysine solution. The concentration of the MPC solution is preferably in a range from 0.001% to 1%, and more preferably, in a range from 0.01% to 0.1%. The concentration of the poly-L-lysine solution is preferably in a range from 0.001 to 0.1%, and more preferably, in a range from 0.005 to 0.015%. The mixing ratio of the MPC solution and the poly-L-lysine solution is preferably in a range from 50:50 to 100:0, and more preferably, in a range from 75:25 to 90:10.

A cell seeding density for forming a spheroid using the culture chamber 10 is not limited. However, the cell seeding density is preferably in a range from 5000 cells/cm$^2$ to 1,000,000 cells/cm$^2$. To form a spheroid having a diameter in a range from 50 μm to 150 μm, it is preferable that 50 to 250 cells are present in 11 area. Accordingly, it is more preferable that the cell seeding density be in a range from 100,000 cells/cm$^2$ to 500,000 cells/cm$^2$. One to 15 days may be required to culture cells to form a spheroid.

Process B: Removing Process

The culture medium is removed with, for example, a Pasteur pipette. It is preferable to remove the total amount of the culture medium used in the spheroid formation process, to thereby eliminate the effect of the serum contained in the culture medium. Additionally, it should be noted that in the process of removing the culture medium, the state in which the spheroids formed in each culture room 11 adhere to the walls 12 of each culture room 11 or the bottom culture surface 14 is maintained. By maintaining the state in which the spheroids adhere to the walls 12 or the bottom culture surface 14, the spheroids are prevented from adhering to spheroids formed in other culture rooms 11. Additionally, if the cells are removed during replacement of test solution or by washing operation for the replacement, a test cannot be conducted. For this reason, it is preferable to allow the cells to adhere to the culture rooms 11.

Process C: Test Solution Addition Process

This process will be described as a process distinct from Process C'.

In the test solution addition process of Process C, one of a test solution and a control solution is added to each well 21. The control solution is used as a comparative example of the example in which the test solution is added.

It is preferable to use a test solution containing no serum so as to eliminate the influence of cytokines contained in a serum on the cells. On the other hand, when the test solution is brought into contact with the cells for 48 hours or more, a serum may be added in a range from 0.1 to 1% to maintain the physiology of the cells.

A solvent for the test solution may have an osmotic pressure of 200 to 315 mOsm/kg and have a buffering action in a pH range of 6.8 to 8.4. Additionally, in order to maintain the physiology of the cells constant, it is preferable to use a solvent containing nutrients such as glucose and amino acid, or vitamins. For example, a mixed culture medium of Dulbecco's modified Eagle medium (DMEM) and Nutrient Mixture F-12 is used to maintain the physiology constant.

Assume that a solution obtained by removing cytokines from the test solution is used as the control solution and the other conditions for the control solution are the same as those for the test solution.

A reference value is set for the cytokine concentration of the test solution, and at least three different types of concentrations based on the reference value are used. A concentration in a range from 0.1 times to 50 times higher than the average value of blood levels of cytokines in a target patient is set as the reference value. On the other hand, when the cytokine concentration in blood of the patient is uncertain, a concentration in a range from 0.1 times to 50 times higher than the average value of blood levels of cytokines in a healthy human is set as the reference value. At least three types of test solutions containing the cytokine at a concentration equal to the reference value, at a concentration that is 10 times higher than the reference value, and at a concentration that is 100 times higher than the reference value, respectively, are used. Based on the blood levels of cytokines in a target patient with disease, the attenuation or induction of the cytochrome P450 due to the cytokine is evaluated to recognize the effect of the cytokine. The evaluation result thus obtained can be used for, for example, adjustment of the dose for the patient. In addition, the use of various types of concentrations based on the reference value makes it possible to evaluate if the attenuation or induction of the cytochrome P450 due to the cytokine depends on the cytokine concentration. Furthermore, regarding a method for setting the reference value, it is preferable to perform the evaluation using the cytokine concentration within a living organism so as to reflect the effect of metabolic enzymes due to the cytokine within a living organism.

Process C': Test Solution Addition Process

In the test solution addition process of Process C', one of the first to third test solutions is added to each well 21. It is preferable to use a test solution containing no serum so as to eliminate the influence of cytokines contained in a serum on the cells. On the other hand, when each test solution is brought into contact with the cells for 48 hours or more, a serum may be added in a range from 0.1 to 1% to maintain the physiology of the cells.

A solvent for each test solution may have an osmotic pressure of 200 to 315 mOsm/kg and have a buffering action in a pH range of 6.8 to 8.4. Additionally, in order to maintain the physiology of the cells constant, it is preferable to use a solvent containing nutrients such as glucose and amino acid, or vitamins. For example, a mixed culture medium of Dulbecco's modified Eagle medium (DMEM) and Nutrient Mixture F-12 is used to maintain the physiology constant.

The cytokine concentrations of the second and third test solutions are determined in advance by the following procedure.

Each of Processes A' to F' is carried out by setting the reference value and using at least three different types of concentrations based on the reference value, and the metabolic function of the cytochrome P450 is analyzed to thereby obtain a measurement value.

A concentration in a range from 0.1 times to 50 times higher than the average value of blood levels of cytokines in a healthy human or cytokines in a patient with disease is set as the reference value. Three types of solutions (or three types of second test solutions) and a solution (first test solution) are prepared. The three types of solutions (or three types of second test solutions) contain the cytokine at a concentration equal to the reference value, at a concentration that is 10 times higher than the reference value, and at a concentration that is 100 times higher than the reference value, respectively, but contain no drug. The solution (first test solution) contains neither the cytokine nor the drug. The solutions thus prepared are brought into contact with spheroid-shaped established hepatocyte cell lines. The metabolic function of the cytochrome P450 of a plurality of established hepatocyte cell lines brought into contact with various types of solutions is measured. Among a plurality of cytokine concentrations obtained as a result of the measurement, a concentration having a value smaller than the measurement value of each cell brought into contact with the first test solution is adopted as the cytokine concentration of the second and third test solutions.

Additionally, in the case of determining the cytokine concentration, it is preferable that the survival rate is 80% or more and the value (second measurement value) of the metabolic function of the cytochrome P450, which is obtained when the spheroid-shaped established hepatocyte cell line is brought into contact with the second test solution for one hour or more and less than 96 hours, be equal to or less than one third, and more preferably, equal to or less than one fifth, of the value (first measurement value) of the metabolic function of the cytochrome P450, which is obtained when the spheroid-shaped established hepatocyte cell line is brought into contact with the first test solution. In the case of determining the cytokine concentration, it is preferable to make an adjustment in such a manner that the drug-metabolizing function of the cytochrome P450 is attenuated depending on the concentration.

An environment in which the effect on the metabolic function of the cytochrome P450 is generated is created by selecting a cytokine concentration having a value smaller than the measurement value of the first test solution. Even in the state where the metabolic function of the cytochrome P450 is attenuated due to the presence of cytokine, the test using the third test solution enables the creation of an environment in which whether or not the drug has an effect on the metabolic function of the cytochrome P450 can be detected. To accurately determine the attenuation and restoration, it is necessary to set the second measurement value to a value significantly smaller than the first measurement value. Assuming variations of about +/−30%, when the average value of the second measurement values is equal to or smaller than 60% of the average value of the first measurement values, it can be determined that the function of drug-metabolizing enzyme is obviously attenuated due to the cytokine. Considering this result, the present inventors have found that the second measurement value is preferably equal to or less than one third of the first measurement value. In this case, however, the attenuation and restoration can be determined by a significance test (for example, t-test), and the preferable range is not limited to this range (equal to or more than one third).

As the concentration of the drug contained in the third test solution, a concentration at which the survival rate of the cells, which are brought into contact with a solution containing the drug at any concentration in a range from one hour to 96 hours, is more than 80% is adopted. If the concentration is too low, the restoration of the cytochrome P450 due to the drug may not be observed. Accordingly, it is preferable to use a test solution having a drug concentration as high as possible within a survival rate range of not less than 80%.

In the test for determining the concentrations of the cytokine and the drug, Processes A to F are carried out in the same manner as in the example or the comparative example.

Process D: Contact Process

The time (contact time) for bringing the test solution or the control solution into contact with the cells is determined depending on the degree of cytotoxicity of cytokines. The cytotoxicity refers to the ability to cause cell death. In Process D, a time for which the cells are brought into contact with the test solution having a maximum cytokine concentration available for the test in the range from one hour to 96 hours and the survival rate is 80% or more is adopted as the contact time. For example, in the case of using three types of concentrations that are equal to the reference value, 10 times higher than the reference value, and 100 times higher than the reference value, respectively, the test solution containing the cytokine at the concentration that is 100 times higher than the reference value is used to measure the survival rate. In Process D', a time for which the cells are brought into contact with the second and third test solutions available for the test in the range from one hour to 96 hours and the survival rate is 80% or more is adopted as the contact time. In the case of determining the cytokine concentration, an appropriate concentration at which the survival rate is 80% or more may be selected.

At any time, when the survival rate is 80% or less, the reference value of the cytokine concentration is set to a low value and a reaction time at which the survival rate is 90% or more is adopted. Any time period can be adopted as long as the time for bringing each test solution into contact with the spheroid-shaped established hepatocyte cell line in Process D' is the same as the contact time for each of the first to third test solutions and the survival rate exceeds 80%.

Figure 9:
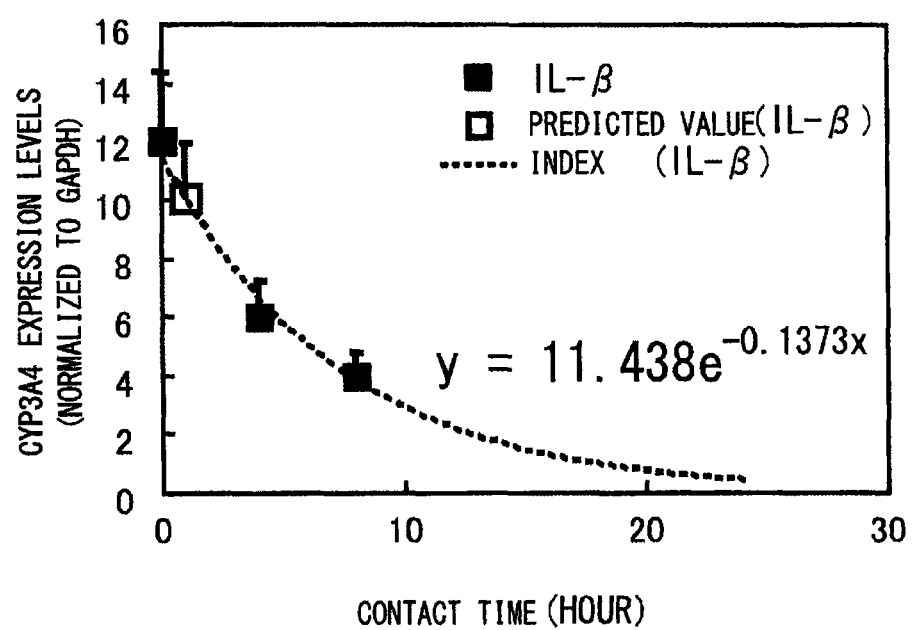
FIG. 9 is a graph showing test results which show the relationship between the length of time for bringing a spheroid-shaped established hepatocyte cell line into contact with a test solution containing a cytokine, and the reactivity of a metabolic function of a cytochrome P450.

FIG. 9 shows the test results which show the relationship between the length of time for bringing the spheroid-shaped established hepatocyte cell line into contact with the test solution containing the cytokine (interleukin-1β), and the reactivity of the cytochrome P450. In the case of bringing the interleukin-1β into contact with the spheroid-shaped established hepatocyte cell line for 0 hours, four hours, and eight hours, the gene expression level of CYP3A4 decreases over time. The error was about 20 to 30%. As shown in FIG. 9, an approximate curve was created to calculate the value for the contact time of one hour. A formula shown in FIG. 9 was used for the approximate curve. It was expected that no significant difference from the value for the contact time of 0 hours would be observed in the case where the error is 20% and the contact time is shorter than one hour. Accordingly, the time for bringing the cells into contact with the cytokine was set to at least one hour. The contact time is preferably as short as possible so as to shorten the evaluation period. This also contributes to a reduction in cost.

The culture medium containing nutrients is used for culture, but the culture medium contains no serum. Accordingly, there is a possibility that the physiology of the cells is reduced. In general, replacement of culture medium is carried out at a frequency at which the nutrients in the culture medium are not completely consumed and waste products are prevented from accumulating and affecting the physiology. For example, it is necessary to replace the culture medium every three or four days. In other words, culture for five or more days is not suitable in terms of maintenance of the bioactivity of cells. For this reason, the cells were brought into contact with the cytokine for 96 hours at maximum.

Process E: Analysis Process

In the analysis process of Process E, the metabolic function of the cytochrome P450 is analyzed using the cells that are brought into contact with the test solution, the control solution, or the first to third test solutions. The first measurement value is obtained by measuring the function of the drug-metabolizing enzyme of the cytochrome P450 of the established hepatocyte cell line brought into contact with the first test solution. Similarly, the second and third measurement values are obtained by measuring the function of the drug-metabolizing enzyme of the cytochrome P450 of the established hepatocyte cell line brought into contact with the second and third test solutions.

As a method for analyzing the cytochrome P450, a technique such as measurement of the gene expression level using a PCR method, protein analysis using a western blotting method, or measurement of the metabolic activity using Liquid Chromatography-tandem Mass Spectrometry (LC/MS/MS) or High performance liquid chromatography (HPLC) may be used Process F: Evaluation Process This process will be described as a process distinct from Process F'.

In the evaluation process of Process F, the determination is made in the following manner based on the value (measurement value) of the metabolic function obtained as a result of analysis in the analysis process in Process E. Assuming that the result obtained by analyzing the cells brought into contact with the test solution is represented as "value T" and the result obtained by analyzing the cells brought into contact with the control solution is represented as "value C", the value of the metabolic function analyzed in Process E is evaluated in the following manner.

When the value T is greater than the value C (value T>value C), it is determined that "the test substance induces the metabolic function of the cytochrome P450". An increase in the value obtained as a result of analyzing the cytochrome P450 shows that the cytokine induces the metabolic function of the cytochrome P450.

On the other hand, when the value T is smaller than the value C (value T<value C), it is determined that "the test substance attenuates the cytochrome P450". A decrease in the value obtained as a result of analyzing the cytochrome P450 shows that the cytokine attenuates the metabolic function of the cytochrome P450.

When the value T and the value C are the same, it is determined that "the test substance has no effect on the cytochrome P450".

Moreover, in the evaluation process, according to the result obtained by analyzing the function of the cytochrome P450 after bringing the cells into contact with the test solutions at three types of concentrations that are equal to the reference value, 10 times higher than the reference value, and 100 times higher than the reference value, respectively, when the function is increased depending on the concentration, it is preferably determined that "the cytokine induces the metabolic function of the cytochrome P450", or when the function is reduced, it is preferably determined that "the cytokine attenuates the metabolic function of the cytochrome P450".

However, even if there is no concentration dependency, when the value of the function of the cytochrome P450 is predominantly high in the case of the test solution containing no cytokine, it may be determined that "the cytokine induces the metabolic function of the cytochrome P450". Alternatively, when the value is predominantly low, it may be determined that "the cytokine attenuates the metabolic function of the cytochrome P450".

As described above, in the evaluation method according to an embodiment, an established hepatocyte cell line of human origin is used and the established hepatocyte cell line is cultured and allowed to proliferate to form a spheroid of a desired size, and the spheroid is brought into contact with a test substance, to thereby evaluate the effect of the cytochrome P450 on the metabolic function. The evaluation of the cytochrome P450 is determined to be one of "attenuation", "induction", and "no effect" as to whether the test substance affects the metabolic activity of the cytochrome P450, based on the measurement value obtained by measuring the metabolic function of the spheroid brought into contact with the test solution or the control solution. The types of the determination result are not limited to "attenuation", "induction", and "no effect", and other types of determination result indicating the effect of the test substance may be used.

Process F': Determination Process

In the determination process of Process F', when the first measurement value is greater than the second measurement value and the second measurement value is smaller than the third measurement value, based on the first to third measurement values analyzed in the analysis process of Process E', it is determined that the drug restores the drug-metabolizing function of the cytochrome P450. This case can be expressed using formulas "first measurement value>second measurement value" and "second measurement value<third measurement value". Especially, when the third measurement value is three times or more than the second measurement value, it is preferably determined that the drug restores the drug-metabolizing function. This is because, as described above, in order to accurately determine the attenuation and restoration, it is necessary that the second measurement value be significantly smaller than the first measurement value.

EXAMPLES

The example and the comparative example will be described below.

1. Preparation of Cells (Spheroid Formation Process)

Example (1-1) Culture Chambers and Cells

Figure 8:
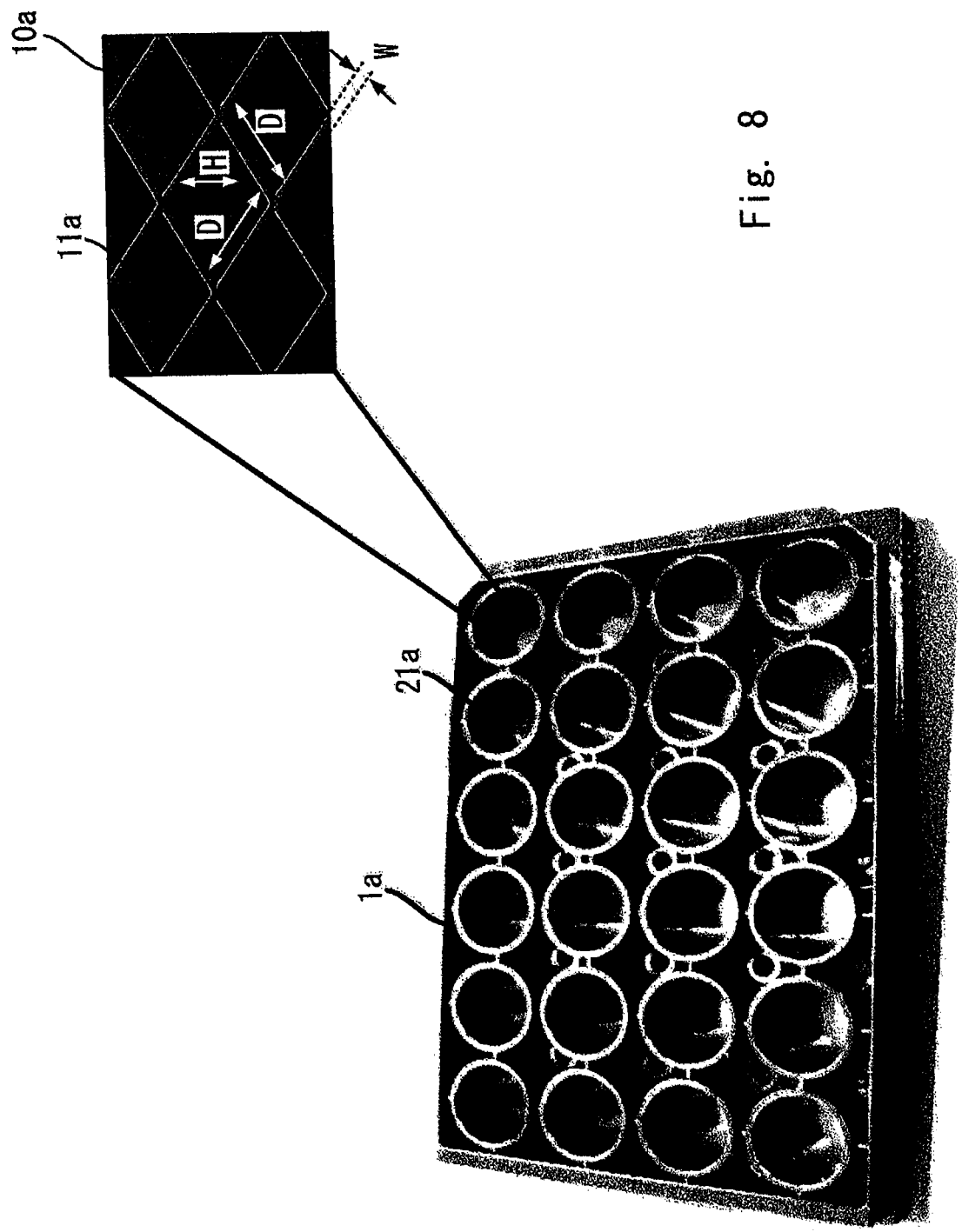
FIG. 8 is a photograph showing an example of the culture plate used in an example.

A culture plate $1a$ including a plurality of wells $21a$ as shown in FIG. 8 was used. A plurality of culture chambers $10a$ are formed on the bottom culture surface of each well $21a$. Each culture chamber $10a$ includes culture rooms $11a$ each having the equivalent diameter D of 200 μm and the height H of 100 μm. The width W of each wall $12a$ is 10 μm.

As cells to be cultured, FLC-4 cells which are established hepatocyte cell lines of Japanese origin were used.

(1-2) Preparation of Culture Chambers

A solution prepared by mixing 0.01% MPC solution and 0.01% poly-L-lysine (produced by SIMGA Corporation) at a ratio of 9:1 was used as a coating agent.

After 0.3 mL of coating solution were injected into each well and was dried in a clean bench.

Before usage, the culture chambers were washed with phosphate-buffered saline (PBS).

(1-3) Cell Culture

As a culture medium, a DMEM/F 12 culture medium containing 10% fetal bovine serum (FBS) was used. A cell suspension was adjusted at a cell seeding density of $16 \times 10^5$ cells/mL.

To each well, 500 µL of cell suspension were added.

The cells were cultured in a $CO_2$ incubator for 10 to 11 days. The culture medium was replaced once every three days.

During replacement of the culture medium, about 100 µL of culture medium were left, instead of removing the total amount of the culture medium, and 500 µL of culture medium were newly added.

Comparative Example

As the culture chamber, a commercially-available 24-well plate having a flat culture surface was used. The cell culture grade was used as the grade for the culture plate.

Except for the above-mentioned conditions, the comparative example was carried out under the same conditions as those for the example.

2A. Test Conditions (the Culture Medium Removing Process, the Test Solution Addition Process, and the Contact Process) for Studying the Evaluation Method In both the example and the comparative example, tests were conducted under the following conditions.

(2A-1) Procedure

The cultured cells were processed in the following procedure.

The total amount of old culture medium was removed from each well by using a pipette (culture medium removing process).

A test solution or a control solution was added to each well (test solution addition process).

The cells were incubated in a $CO_2$ incubator for eight hours, 24 hours, or 48 hours at 37° C. (contact process).

(2A-2) Adjustment of the Test Solution and the Control Solution

The test solution was obtained in such a manner that the cytokine was dissolved at each concentration shown in Table 1 in a DMEM/F12 solution (DMEM/E12 FBS(−)) containing no serum.

A DMEM/F12 solution containing no serum was used as the control solution, and the cytokine concentration was set to 0 mM.

(2A-3) Analysis

The metabolic function of CYP3A4 was analyzed by analysis methods shown in Table 1. As for TNF-α, the functions of CYP3A4 as well as CYP2C9 were analyzed.

TABLE 1

| Cytokine | Analysis Method | Reaction Time (hour) | Cytokine Concentration | Unit |
|---|---|---|---|---|
| Epidermal Growth Factor (EGF) | Gene Analysis | 24 | 0, 0.1, 1, 10 | ng/mL |
| Heparin-binding EGF-like growth factor (HB-EGF) | Gene Analysis | 24 | 0, 1, 10, 100 | ng/mL |
| Interleukin (IL)-1β | Gene Analysis | 8 | 0, 1, 10, 200 | pg/mL |
| Tumor Necrosis Factor (TNF)-α | Gene Analysis | 24 | 0, 0.1, 1, 10 | ng/mL |
| Interleukin (IL)-6 | Gene Analysis | 24 | 0, 0.1, 1, 10 | ng/mL |
|  | Western Blotting Method | 48 | 0, 0.1, 1, 10 | ng/mL |
|  | Activity Measurement (HPLC Method) | 24 | 0, 0.1, 1, 10 | ng/mL |

2B. Test Conditions for Studying the Cytokine Concentration of Each Test Solution to Study the Screening Method The cytokine concentration of each test solution was studied in the following procedure for both the example and the comparative example.

(2B-1) Preparation of Test Solutions

Epidermal Growth Factor (EFG) was used as the cytokine.

DMEM/F12 (DMEM/E12 FBS(−)) containing no serum was used as a solvent for each test solution.

To study the cytokine concentrations of the second and third test solutions, test solutions respectively having EGF concentrations of 0.1 ng/mL, 1 ng/mL, and 10 ng/mL were prepared. Note that the cells were cultured in each test solution in advance to obtain a cell survival rate, and it was confirmed that the cell survival rate at these concentrations was 80% or more.

(2B-2) Procedure

The cultured cells were processed in the following procedure.

The total amount of old culture medium was removed from each well by using a pipette (culture medium removing process).

Each test solution for studying the cytokine concentration was added to each well (test solution addition process).

The cells were incubated for eight hours, 24 hours, or 48 hours at 37° C. in a $CO_2$ incubator (contact process).

The analysis was carried out by the western blocking method.

(2B-3) Results

Figure 10:
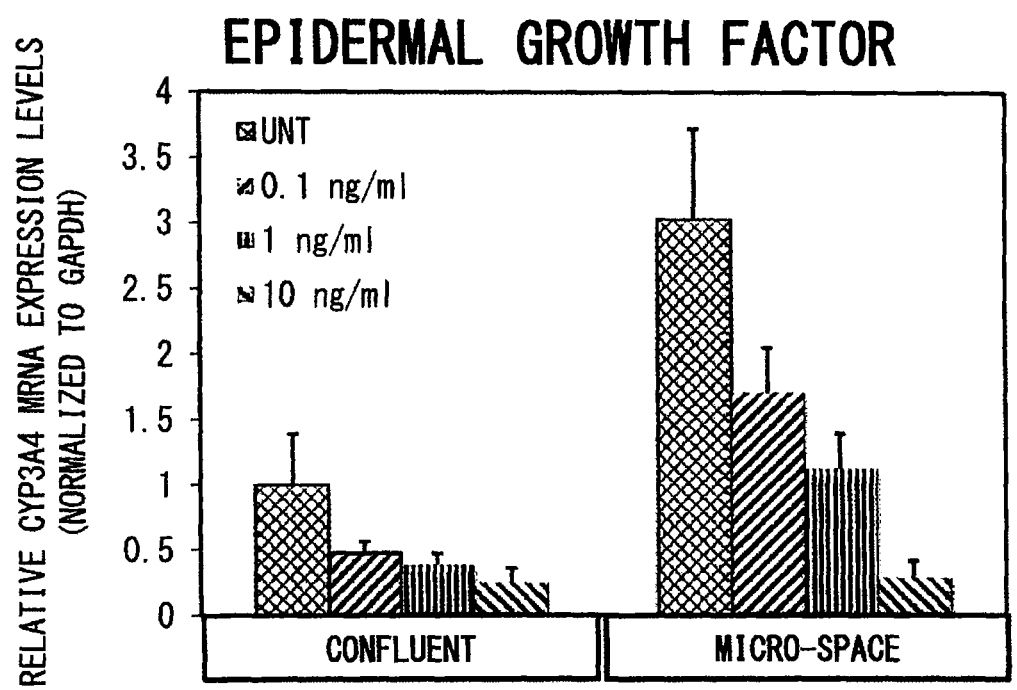
FIG. 10 is a graph showing results of measurement of gene expression levels of CYP3A4 when an epidermal growth factor is added.

FIG. 10 shows test results obtained as a result of studying the cytokine concentration of each test solution. In the figure, the example is represented by "MICRO-SPACE" and the comparative example is represented by "CONFLUENT". The results obtained by analyzing the EGF concentration and the amount of CYP3A4 protein for each case of 0, 0.1, 1, and 10 ng/mL by the western blotting method are represented by bands.

In the example, since the bands are thinned as the EGF concentration increases, it is confirmed that the function of CYP3A4 decreases depending on the concentration. As the cytokine concentration of each test solution, a concentration of 10 ng/mL was adopted for each of the second and third test solutions.

In the comparative example, the concentration dependency was not confirmed. To compare the comparative example with the example, the concentration of 10 ng/mL was adopted.

Test Conditions (the Culture Medium Sucking Process, the Test Solution Addition Process, and the Contact Process)

In both the example and the comparative example, tests were conducted under the following conditions.

(2B-4) Test 1

The test was carried out to compare the values of the drug-metabolizing enzyme function of the cytochrome P450 when the first test solution and the second test solution were brought into contact with the spheroid-shaped established hepatocyte cell line.

For the test, 2. Results of the tests conducted to study the concentration of the test solutions were used. The test procedure has been described above.

(2B-5) Test 2

The test was carried out to compare the values of the function of the drug-metabolizing enzyme of the cytochrome P450 when the first to third test solutions were brought into contact with the spheroid-shaped established hepatocyte cell line.

The comparative example was not carried out because the results of Test 1 showed that the test result for the first test solution and the test result for the second test solution were substantially the same and the conditions were not met. The results of Test 1 will be described later.

Epidermal Growth Factor (EFG) was used as the cytokine.

Gefitinib was used as the drug.

DMEM/F12 (DMEM/E12 FBS(−)) containing no serum was used as a solvent for each test solution.

As the cytokine concentration, 10 ng/mL was adopted.

The first test solution contains 0 mM of EGF and 0 mM of Gefitinib.

The second test solution contains 10 ng/mL of EGF and 0 mM of Gefitinib.

The third test solution concentration contains 10 ng/mL of EGF and 5 µM of Gefitinib.

The cultured cells are processed in the following procedure.

The total amount of old culture medium was removed from each well by using a Pasteur pipette (culture medium removing process).

The first to third test solutions were added to each well (test solution addition process).

The cells were incubated in the $CO_2$ incubator for eight hours, 24 hours, or 48 hours, at 37° C. (contact process).

An analysis was made by gene analysis.

3. Analysis Method (3-1) Metabolic Activity Measurement Method

After removing the supernatant obtained after the reaction, a solution for analysis containing 50 µM of triazolam was added and the resulting mixture was incubated for 24 hours at 37° C. under the condition of 5% $CO_2$. After 150 µL, of collected culture medium was transferred to a test tube and 50 µL of oxazepam (0.2 µg/mL in methanol) was added as an internal standard material, 300 µL of acetonitrile (Wako Pure Chemical Industries, Ltd.) cooled with ice were added and stirred, and the solution was subjected to centrifugal separation (3000 r.p.m., 10 minutes, 4° C.) to thereby cause protein to settle out. After that, a vacuum evaporator was used to evaporate acetonitrile, and 70 µL of solution obtained by filtering the supernatant were injected in HPLC. Samples obtained by adding 10 µL of methanol solutions each containing 10, 40, 80, 160, and 320 pmol of α-hydroxytriazolam and 4-hydroxytriazolam into 130 µL of culture medium were used as samples for calibration curve. Each of α-hydroxytriazolam and 4-hydroxytriazolam was determined by HPLC. The calibration curve was obtained by performing linear regression using least-squares method on the ratio of the peak height of α-hydroxytriazolam and the peak height of 4-hydroxytriazolam with respect to the internal standard material of each sample for calibration curve.

(3-2) Gene Analysis Method (RT-qPCR)

In an RNA extraction, one sample corresponding to two wells 21a of the culture plate 1a was extracted according to the protocol of NucleoSpin® RNAII (Macherey-Nagel). Only the portion to be subjected to Dnase treatment was modified, and DNaseI recombinant, RNase-free (Roche, Branchburg, N.J., USA) was used. The total RNA underwent reverse transcription reaction using High-Capacity cDNA Reverse Transcription Kits (Applied. Biosystems, Foster City, Calif., USA) and an attached random hexamer primer, and the first strand cDNA was synthesized.

The analysis was made using a total amount of 20 µL of reaction liquid containing 9.6 µL of EagleTaq Master Mix with ROX (Roche, Branchburg, N.J., USA), 0.96 µL of 20× Assays-on-Demand™ Gene Expression Assay Mix (Applied Biosystems), 7.1 µL of sterilized MiliQ water, and 1.8 µL of cDNA diluted by a factor of 5, and the reaction liquid was measured by Real-time PCR.

(3-3) Western Blotting Method (WB)

The cells corresponding to three to six wells were sonicated by a Lysis buffer containing 0.1% protease inhibitor cocktail and 1 mM PMSF (Phenylmethyl sulfonyl fluoride). After that, 12000 g of the sample were centrifuged for 15 minutes, and the supernatant was used as an all cell extract. The all cell extract (10-15 µg/lane) thus obtained was separated by electrophoresis of 10% SDS-polyacrylamide gel and was then transcripted onto a nitrocellulose membrane for two hours at a voltage of 54 V. The nitrocellulose membrane subjected to the transcription was shook at room temperature for one hour and was subjected to blocking using PBS (PBST) containing 0.05% Tweem20 in which 5% skim milk was added. An anti-human CYP3A antibody (monoclonal, BD Gentest) diluted 6000 times with PBST containing 3% BSA was used as a primary antibody, and the primary antibody was incubated overnight at 4° C. An anti-mouse IgG-peroxydase antibody (Sigma-Aldrich) diluted 5000 times with PBST containing 3% BSA was used as a secondary antibody, and the secondary antibody was shook at room temperature for one hour. ImmunoStar LD (Wako Pure Chemical Industries, Ltd.) was used as protein and was detected using LAS-1000 plus (Fujifilm, Tokyo).

4. Test Results

FIGS. 10 to 18 show tests results obtained as a result of studying the evaluation method. In the figures, the example is represented by "MICRO-SPACE" and the comparative example is represented by "CONFLUENT". A case (non-addition group) in which the control solution was added to the cells is represented by "UNT" (Untreated) and a case in which the test solution was added to the cells is represented by a concentration of added cytokines (for example, 0.1 ng/mL). The results shown in FIGS. 10 to 15 are values obtained by adding a standard deviation to the average value obtained as a result of experiments separately carried out three times in duplicate.

In the operation in which the test results shown in FIG. 10 were obtained, FLC-4 cells were cultured for 10 days. The control solution or the test solution containing 0.1 ng/mL, 1 ng/mL, and 10 ng/mL of epidermal growth factor (EFG) was added to the cultured cells, and the cells were cultured for 24 hours. FIG. 10 shows the results of analysis of CYP3A4 mRNA expression levels by RT-qPCR for the cultured cells at four types of EGF concentrations.

Figure 11:
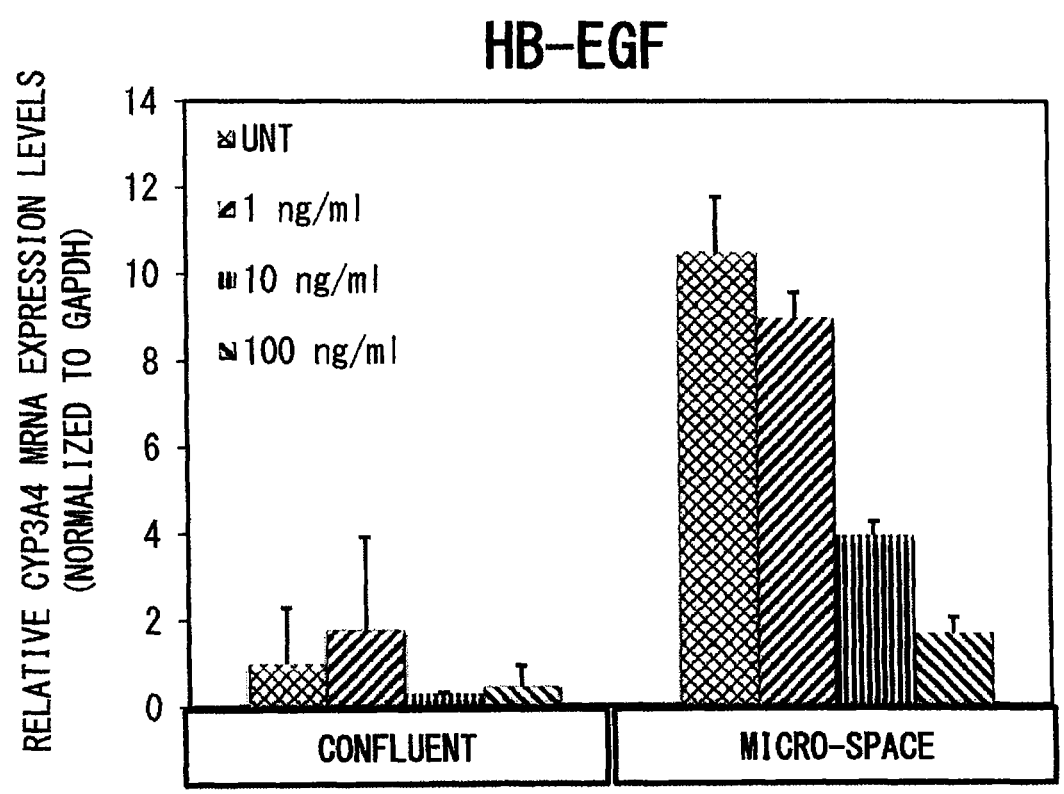
FIG. 11 is a graph showing results of measurement of gene expression levels of CYP3A4 when a heparin-binding epidermal growth factor-like growth factor is added.

In the operation in which the test results shown in FIG. 11 were obtained, FLC-4 cells were cultured for 10 days. The control solution or the test solution containing 1 ng/mL, 10 ng/mL, and 100 ng/mL heparin-binding epidermal growth factor-like growth factor (HB-EGF) was added to the cultured cells, and the cells were cultured for 24 hours. FIG. 11 shows the results of analysis of CYP3A4 mRNA expression levels by RT-qPCR for the cultured cells at four types of HB-EGF concentrations.

Figure 12:
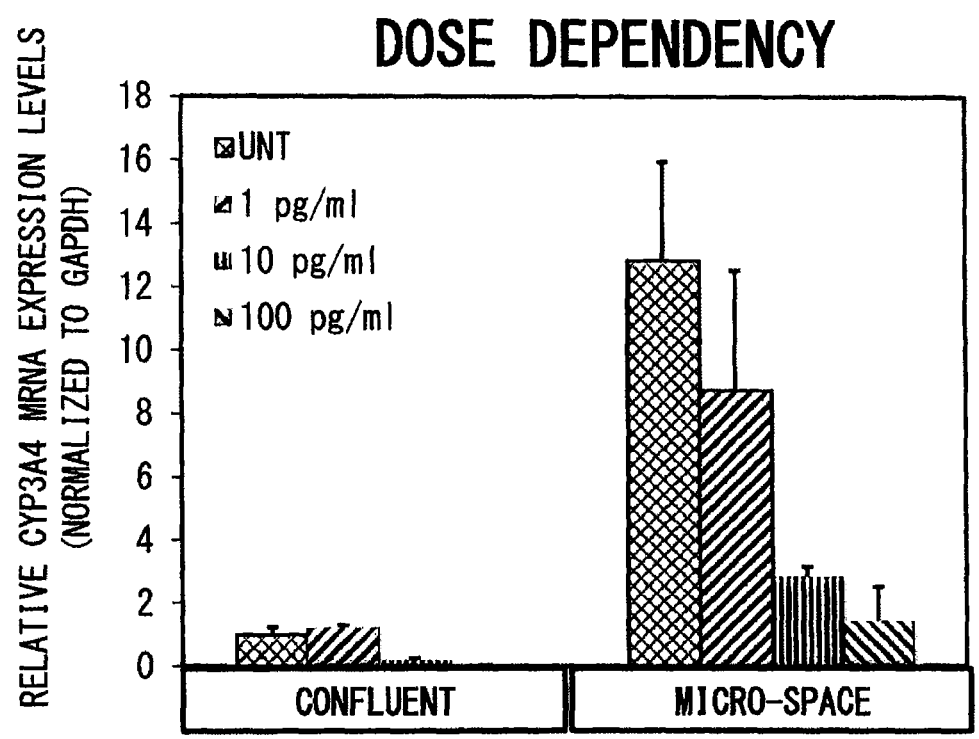
FIG. 12 is a graph showing results of measurement of gene expression levels of CYP3A4 when interleukin-1β is added.

In the operation in which the test results shown in FIG. 12 were obtained, FLC-4 cells were cultured for 10 days. The control solution or the test solution containing 1 ng/mL, 10 ng/mL, and 100 ng/mL of interleukin-1β (IL-1β) was added to the cultured cells, and the cells were cultured for 24 hours. FIG. 12 shows the results of analysis of CYP3A4 mRNA expression levels by RT-qPCR for the cultured cells at four types of IL-1β concentrations.

Figure 13:
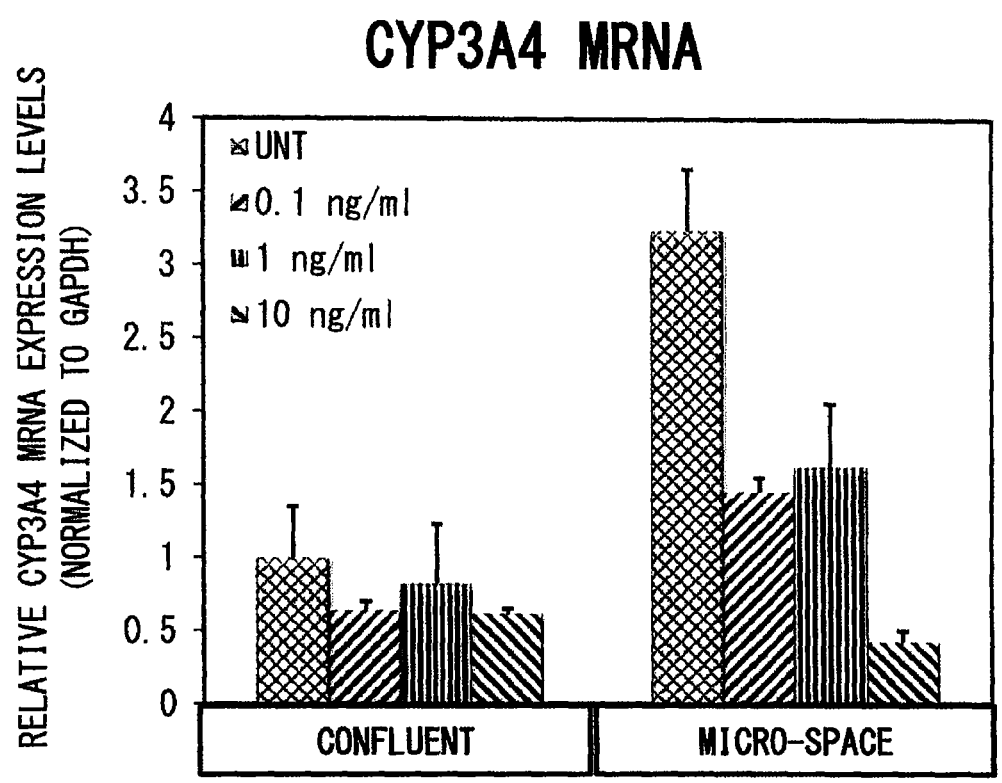
FIG. 13 is a graph showing results of measurement of gene expression levels of CYP3A4 when a tumor necrosis factor is added.
Figure 14:
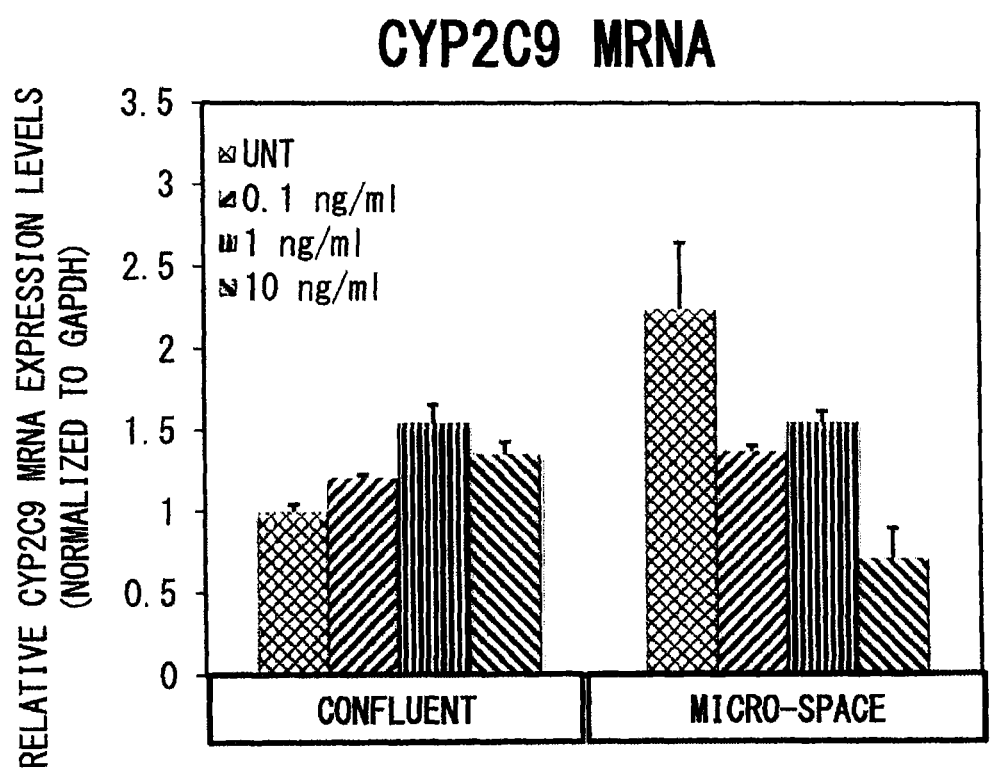
FIG. 14 is a graph showing results of measurement of gene expression levels of CYP2C9 when a tumor necrosis factor is added.

In the operation in which the test results shown in FIGS. 13 and 14 were obtained, FLC-4 cells were cultured for 10 days. The control solution or the test solution containing 0.1 ng/mL, 1 ng/mL, and 10 ng/mL of tumor necrosis factor-α (TNF-α) was added to the cultured cells, and the cells were cultured for 24 hours. FIGS. 13 and 14 show the results of analysis of mRNA expression levels of CYP3A4 (FIG. 13) and CYP2C9 (FIG. 14) by RT-qPCR for the cultured cells at four types of EGF concentrations.

Figure 15:
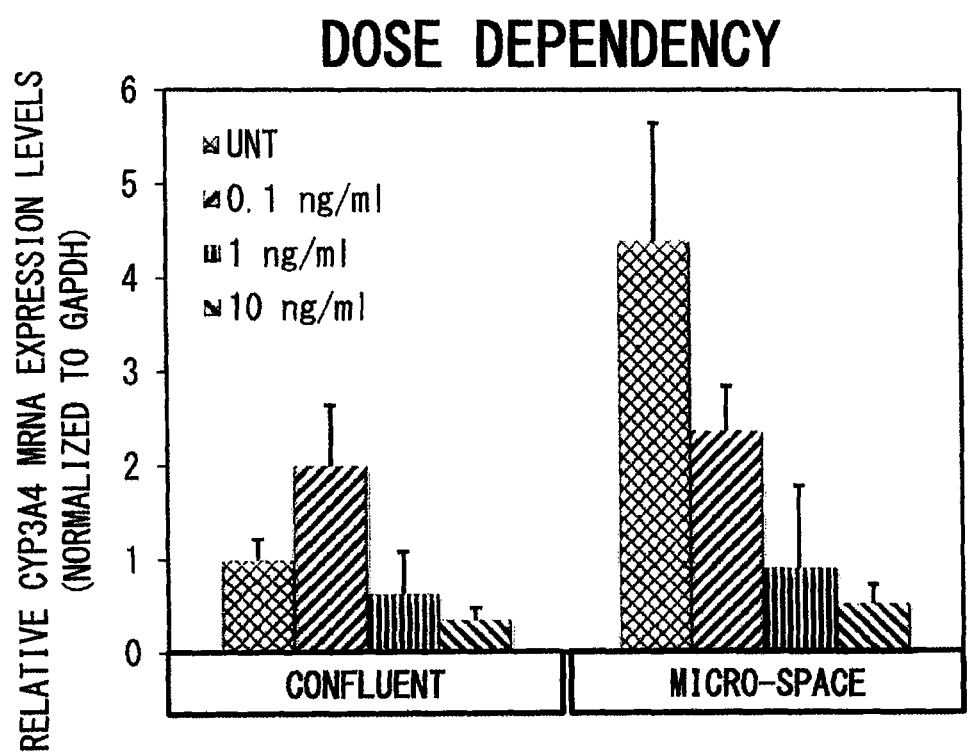
FIG. 15 is a graph showing results of measurement of gene expression levels of CYP2C9 when interleukin-6 is added.

In the operation in which the test results shown in FIG. 15 were obtained, FLC-4 cells were for 10 days. The control solution or the test solution containing 0.1 ng/mL, 1 ng/mL, and 10 ng/mL of interleukin-6 (IL-6) was added to the cultured cells, and the cells were cultured for 24 hours. FIG. 15 shows the results of analysis of CYP3A4 mRNA expression levels by RT-qPCR for the cultured cells at four types of IL-6 concentrations.

Figure 16:
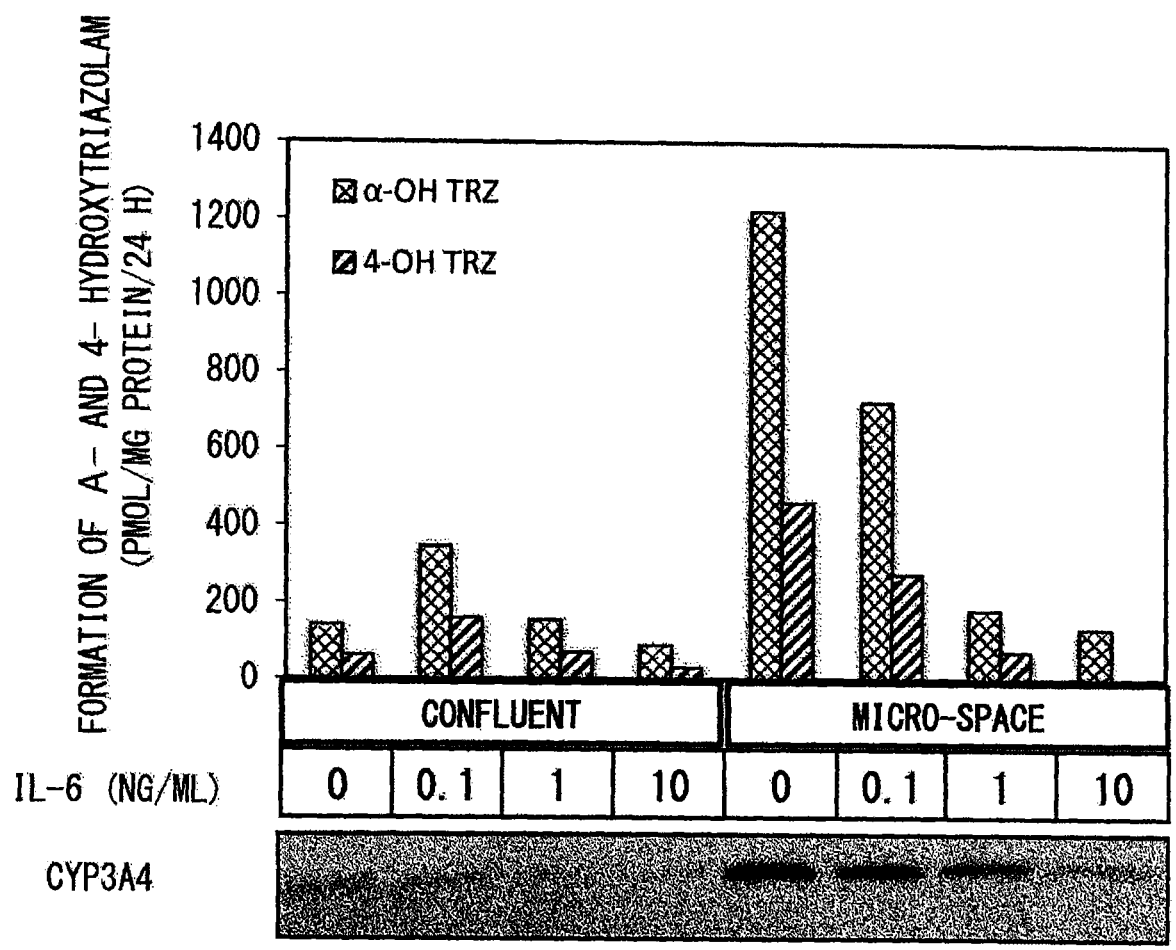
FIG. 16 is a graph showing test results of the amount of protein and metabolic activity of CYP3A4 in an interleukin-6 test.

In the operation in which the test results shown in FIG. 16 were obtained, FLC-4 cells were cultured for 10 days. The control solution or the test solution containing 0.1 ng/mL, 1 ng/mL, and 10 ng/mL of IL-6 was added to the cultured cells, and the cells were cultured for 48 hours. After that, 50 μg/mL of triazolam was added, and the cells were cultured for 24 hours. FIG. 15 shows the results of analysis of the amount of CYP3A4 protein by the western blotting method for the cultured cells at four types of IL-6 concentrations.

FIG. 17 shows the results of the test on the concentration dependency of cytokines.

FIG. 18 shows the result of determination of the test results based on the technique described in the evaluation process. In FIG. 18, the item "effect of cytokine" indicates the test results determined based on the comparison between the cells (cytokine-added group) to which the test solution was added, and the cells (non-addition group) to which the control solution was added, and the item "concentration dependency" indicates the test results obtained as a result of determining the concentration dependency based on the test results for different cytokine concentrations. In FIG. 18, "-" indicates that a determination could not be made.

In the example, it was confirmed that in each cytokine, the CYP3A4 gene expression levels were reduced predominantly with respect to the control (cytokine concentration of 0 mM).

In the comparative example, the CYP3A4 gene expression levels were not reduced predominantly with respect to the control (cytokine concentration of 0 mM).

The cytokines used in the above-mentioned example are illustrated by way of example, and other types of cytokines can also be used for the evaluation method according to an embodiment.

The results obtained as a result of studying the screening method are shown below.

Results of Test 1

Figure 19:
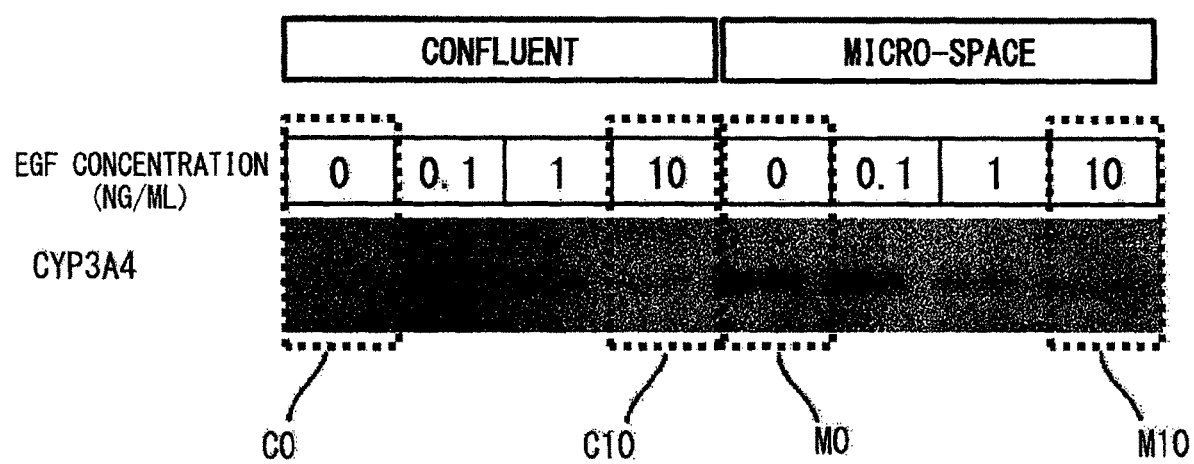
FIG. 19 is a diagram showing test results of reviewing the relationship between the concentration of cytokines in a test solution and the amount of CYP3A4 protein.

A determination was made using the test results obtained as a result of studying the test solution concentrations shown in FIG. 19. Referring to the test results shown in FIG. 19, both the example and the comparative example are determined by comparing the result of the first test solution having an EGF concentration of 0 ng/mL with the result of the second test solution having an EGF concentration of 10 ng/mL (four bands surrounded by dotted lines in FIG. 19, CYP3A4, and the amount of protein). Assume that the amount of CYP3A4 protein obtained when the first test solution is brought into contact with the spheroids is M0 in the example and C0 in the comparative example and the amount of CYP3A4 protein obtained when the second test solution is brought into contact with the spheroids is M10 in the example and C10 in the comparative example.

In the example, the band representing the second test solution is lighter than the band representing the first test solution. In other words, M0 is greater than M10 (M0>M10).

On the other hand, in the comparative example, the difference between the band representing the first test solution and the band representing the second test solution cannot be detected. In other words, C0 and C10 are nearly equal (C0≈C10).

Results of Test 2

Figure 20:
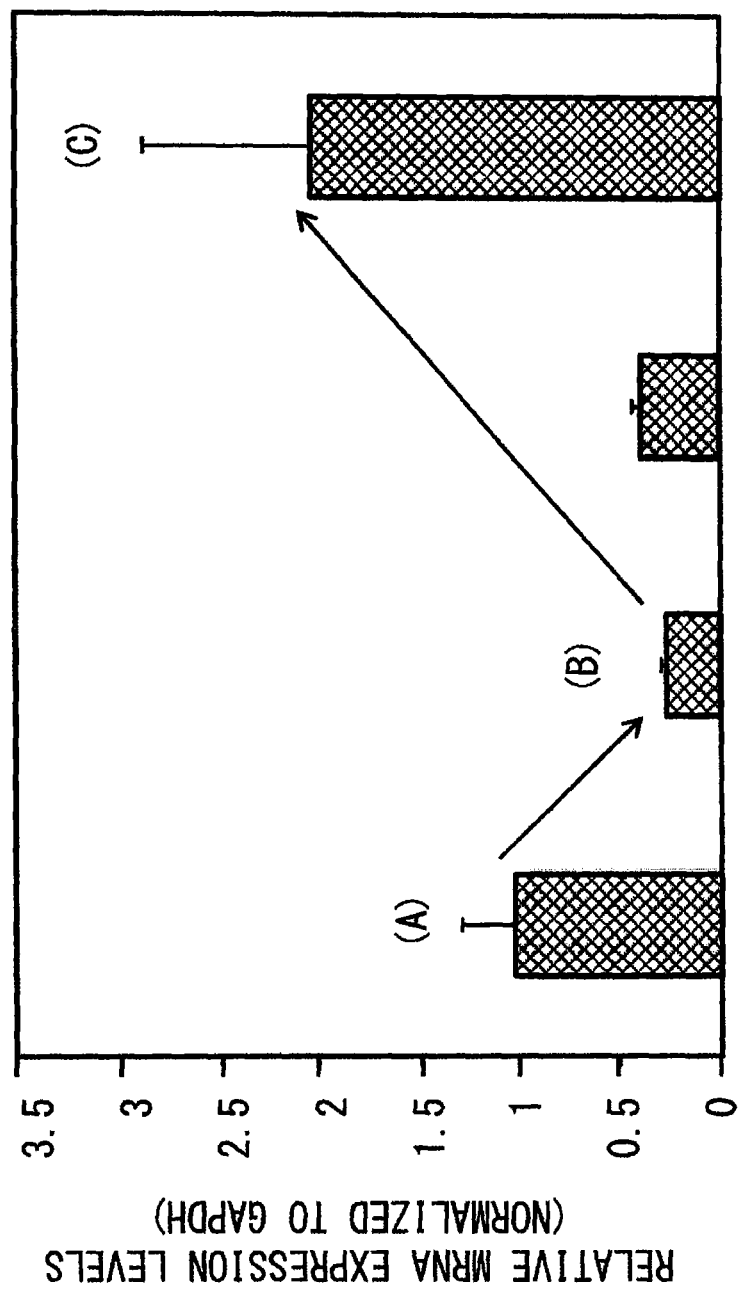
FIG. 20 is a graph showing mRNA expression levels of CYP3A4 when first to third test solutions are brought into contact with spheroids.

FIG. 20 shows the results of analysis of CYP3A4 mRNA expression levels by RT-qPCR when the first to third test solutions are brought into contact with the spheroid-shaped established hepatocyte cell lines. In FIG. 20, the case (A) indicates the CYP3A4 mRNA expression level for the first test solution; the case (B) indicates the CYP3A4 mRNA expression level for the second test solution; and the case (C) indicates the CYP3A4 mRNA expression level for the third test solution. The results in FIG. 20 show that the value of the metabolic function of CYP3A4 in the case of using the second test solution (cytokine-containing and drug-free) is lower than that in the case of using the first test solution (cytokine-free and drug-free). Additionally, the value of the metabolic function of CYP3A4 in the case of using the third test solution (cytokine-containing and drug-containing) is three times higher than that in the case of using the second test solution. Based on the above results, it can be determined that the drug restores the drug-metabolizing function of the cytochrome P450.

The cytokine used in the above examples is illustrated by way of example only. Needless to say, the screening method according to an embodiment of the invention can be applied to other types of cytokines.

The present invention is not limited to the embodiments described above. The components of the embodiments described above can be changed, added, or converted to contents that can be easily conceived by those skilled in the art within the scope of the present invention.

This application is based upon and claims the benefit of priority from Japanese patent application No. 2012-213977, filed on Sep. 27, 2012, and Japanese patent application No. 2012-213978, filed on Sep. 27, 2012, the disclosure of which is incorporated herein in its entirety by reference.

REFERENCE SIGNS LIST 1, 1a CULTURE PLATE
8 CELL
9 SPHEROID 10, 10a CULTURE CHAMBER
11, 11a CULTURE ROOM
12 WALL
13 BOTTOM PORTION
14 BOTTOM CULTURE SURFACE
21, 21a WELL
22 PARTITION

The invention claimed is:

1. A method for screening a drug which interacts with a cytokine, comprising:
    preparing a first test solution containing neither the cytokine nor the drug, a second test solution containing the cytokine and not containing the drug, and a third test solution containing both the cytokine and the drug;
    seeding, in each well of a culture plate having at least one well, cells of an established hepatocyte cell line in a culture medium, wherein each well of the culture plate has a plurality of culture rooms;
    culturing the cells of the established hepatocyte cell line and forming, in at least one of the plurality of culture rooms in each well, a spheroid of the cells;
    removing the culture medium from each well;
    adding one of the first test solution, the second test solution, or the third test solution to each well;
    bringing one of the first test solution, the second test solution, or the third test solution into contact with the spheroid of the established hepatocyte cell line in at least one culture room in each well for one hour or more and less than 96 hours, wherein adding the first test solution, the second test solution, or the third test solution to each well brings the first test solution, the second test solution, or the third test solution into contact with the spheroid(s) in each well to which the first test solution, the second test solution, or the third test solution has been added;
    obtaining a first measurement value of cytochrome P450 by measuring a value of a cytochrome P450 of the established hepatocyte cell line brought into contact with the first test solution, and obtaining second and third measurement values of cytochrome P450 by measuring the value of the cytochrome P450 of the established hepatocyte cell line brought into contact with the second and third test solutions, respectively, wherein measuring the value of the cytochrome P450 comprises measuring a value selected from the group consisting of a metabolic activity level of cytochrome P450 in the cell, a gene expression level of cytochrome P450 in the cell, an amount of cytochrome P450 protein in the cell, and combinations thereof; and
    determining that the drug restores a drug-metabolizing function of the cytochrome P450, when the first measurement value is greater than the second measurement value and the third measurement value is three times greater than the second measurement value;
    wherein the third test solution contains the drug at a concentration at which a survival rate of the spheroid of the established hepatocyte cell is more than 80%, when the established hepatocyte cell is brought into contact with the drug at the concentration in a range from one hour to 96 hours;
    wherein each culture room has an equivalent diameter in a range from 50 μm to 500 μm, which is a range equal to or more than 1 times to 5 times the diameter of the spheroid of the established hepatocyte cell line in the culture room, a height that is 0.3 to 1 times the equivalent diameter, a contact angle of a culture surface equal to or less than 45 degrees, and walls partitioning the culture room with each wall having a width in the range of 2 μm to 50 μm;
    wherein an average value of a diameter of the spheroid of the established hepatocyte cell line formed in a culture room is equal to or more than 50 μm and less than 200 μm; and
    wherein a number N2 is a number of spheroids included in all spheroids present in one well, wherein considering a correlation between a size of a diameter of each spheroid and the number of existing spheroids, the number N2 is a number of spheroids present in a range from a minimum diameter D2 to a maximum diameter D3 among a plurality of diameters corresponding to half of a number N1 (N1/2), wherein the number N1 is a number of the existing spheroids included in all the spheroids present in the one well and having a diameter D1, and the number N2 of spheroids accounts for 70% or more of the total number of spheroids in the one well.

2. The screening method according to claim 1, wherein a solvent for the test solution is a serum-free culture medium.

3. The screening method according to claim 1, wherein a concentration of the cytokine of the second and third test solutions is selected from among at least three concentrations of the cytokine at which the second measurement value of cytochrome P450 is smaller than the first measurement value of cytochrome P450, and wherein the at least three concentrations of the cytokine are being equal to a reference concentration, 10 times higher than the reference concentration, and 100 times higher than the reference concentration, respectively, the reference concentration being a cytokine concentration in a range from equal to or more than 0.1 times higher to 50 times higher than a blood level of the cytokine secreted from a patient with a disease.

4. The screening method according to claim 1, wherein in forming the spheroid, the culture medium contains 10% serum.

* * * * *

UNITED STATES PATENT AND TRADEMARK OFFICE
CERTIFICATE OF CORRECTION

PATENT NO. : 10,677,783 B2
APPLICATION NO. : 14/431986
DATED : June 9, 2020
INVENTOR(S) : Kaoru Kobayashi et al.

Page 1 of 1

It is certified that error appears in the above-identified patent and that said Letters Patent is hereby corrected as shown below:

On the Title Page

On page 2, in Column 1, item (56), Other Publications, Line 22, delete "ldenshi" and insert -- Idenshi --, therefor.

In the Claims

In Column 28, Line 43 (Approx.), Claim 3, after "are" delete "being".

Signed and Sealed this
Eighth Day of September, 2020

Andrei Iancu
*Director of the United States Patent and Trademark Office*